US009226771B2

(12) United States Patent
Tycast et al.

(10) Patent No.: US 9,226,771 B2
(45) Date of Patent: *Jan. 5, 2016

(54) MEDICAL DEVICE FOR PROVIDING PORT-LIKE ACCESS TO A MAMMALIAN URINARY SYSTEM AND METHODS OF INSERTING AN UTILIZING THE SAME

(71) Applicant: Tycast Technologies, LLC, Anoka, MN (US)

(72) Inventors: Frank J. Tycast, Anoka, MN (US); James F. Tycast, West Linn, OR (US)

(73) Assignee: Tycast Technologies, LLC, Anoka, MN (US)

( * ) Notice: Subject to any disclaimer, the term of this patent is extended or adjusted under 35 U.S.C. 154(b) by 129 days.

This patent is subject to a terminal disclaimer.

(21) Appl. No.: 13/887,137

(22) Filed: May 3, 2013

(65) Prior Publication Data

US 2014/0148648 A1    May 29, 2014

Related U.S. Application Data

(63) Continuation-in-part of application No. 13/594,523, filed on Aug. 24, 2012, now Pat. No. 8,870,852.

(51) Int. Cl.
*A61B 17/34* (2006.01)
*A61M 25/10* (2013.01)
(Continued)

(52) U.S. Cl.
CPC ......... *A61B 17/3423* (2013.01); *A61J 15/0015* (2013.01); *A61J 15/0042* (2013.01);
(Continued)

(58) Field of Classification Search
CPC .......... A61B 17/3423; A61M 25/0017; A61M 25/01; A61M 39/0247; A61M 2025/0191; A61M 2210/1085; A61M 2039/0276; A61M 2039/0279; A61M 2039/0288; A61M 2039/0297; A61M 25/1025; A61M 2025/0233; A61M 25/02; A61M 25/04; A61M 25/10; A61M 25/1018; A61M 25/10181; A61M 25/10184; A61M 25/10185; A61J 5/0015; A61J 15/0042; A61J 15/0053; A61J 15/0065; A61J 15/0092; A61J 15/007
See application file for complete search history.

(56) References Cited

U.S. PATENT DOCUMENTS 3,938,521 A * 2/1976 Ritota et al. .................. 604/328
4,863,438 A   9/1989 Gauderer et al.
(Continued)

FOREIGN PATENT DOCUMENTS

GB    2428198 A    1/2007
WO    9004431 A1   5/1990

OTHER PUBLICATIONS

International Searching Authority, The International Search Report and the Written Opinion for PCT/US2013/056027, Nov. 18, 2013, 15 pages.
(Continued)

*Primary Examiner* — Adam Marcetich
(74) *Attorney, Agent, or Firm* — Merchant & Gould P.C.

(57) ABSTRACT

A medical device for providing direct port-like endoscopic access to the urinary bladder, or other orifice, of a patient and a method of utilizing and inserting the medical device. The medical device can include a hollow tube with a main channel and a separate channel, a cap with an inflation port and a hollow flexible stem fluidly connecting the inflation port and the separate channel. A method can include inserting a needle above the pubic symphysis of a mammal, threading a guide wire through the needle, removing the needle and inserting the medical device. The method can optionally include determining measuring the depth between the skin surface of the patient's suprapubic region and urinary bladder.

17 Claims, 33 Drawing Sheets

(51) Int. Cl.

| | |
|---|---|
| *A61M 25/14* | (2006.01) |
| *A61J 15/00* | (2006.01) |
| *A61M 25/00* | (2006.01) |
| *A61M 25/01* | (2006.01) |
| *A61M 39/02* | (2006.01) |

(52) U.S. Cl.
CPC ......... *A61J15/0065* (2013.01); *A61J 15/0073* (2013.01); *A61J 15/0092* (2013.01); *A61M 25/0017* (2013.01); *A61M 25/01* (2013.01); *A61M 25/1018* (2013.01); *A61M 25/10181* (2013.11); *A61M 25/10184* (2013.11); *A61M 25/10185* (2013.11); *A61M 39/0247* (2013.01); *A61M 2025/0191* (2013.01); *A61M 2039/0276* (2013.01); *A61M 2039/0279* (2013.01); *A61M 2039/0288* (2013.01); *A61M 2039/0297* (2013.01); *A61M 2210/1085* (2013.01)

(56) References Cited

U.S. PATENT DOCUMENTS

| | | | |
|---|---|---|---|
| 5,007,897 A | 4/1991 | Kalb et al. | |
| 5,007,900 A | 4/1991 | Picha et al. | |
| 5,114,398 A | 5/1992 | Trick et al. | |
| 5,125,897 A | 6/1992 | Quinn et al. | |
| 5,306,226 A | 4/1994 | Salama | |
| 5,336,203 A | 8/1994 | Goldhardt et al. | |
| 5,556,385 A | 9/1996 | Andersen | |
| 5,749,826 A | 5/1998 | Faulkner | |
| 5,817,067 A | 10/1998 | Tsukada | |
| 5,891,113 A | 4/1999 | Quinn | |
| 7,625,355 B2 | 12/2009 | Yu | |
| 2005/0033268 A1 | 2/2005 | Decaria | |
| 2009/0200186 A1 | 8/2009 | Nestenborg et al. | |
| 2010/0298857 A1 | 11/2010 | Zook et al. | |
| 2012/0143123 A1* | 6/2012 | Agnew | 604/28 |

OTHER PUBLICATIONS

Bennett et al.; "The Gastrostomy Button as a Catheterizable Urinary Stoma: A Pilot Study," American Urological Association Copyright 2003, vol. 170, 832-834, 3 pages.

De-Badiola et al.; "New Application of the Gastrostomy Button for Clinical and Urodynamic Evaluation before Vesicostomy Closure," The Journal of Urology, American Urological Association Copyright 1996, vol. 156, 618-620, 3 pages.

Milliken et al.; "Cystostomy Button for Bladder Drainage in Children," The Journal of Urology®, American Urological Association Copyright 2007, vol. 178, 2604-2606, 3 pages.

\* cited by examiner

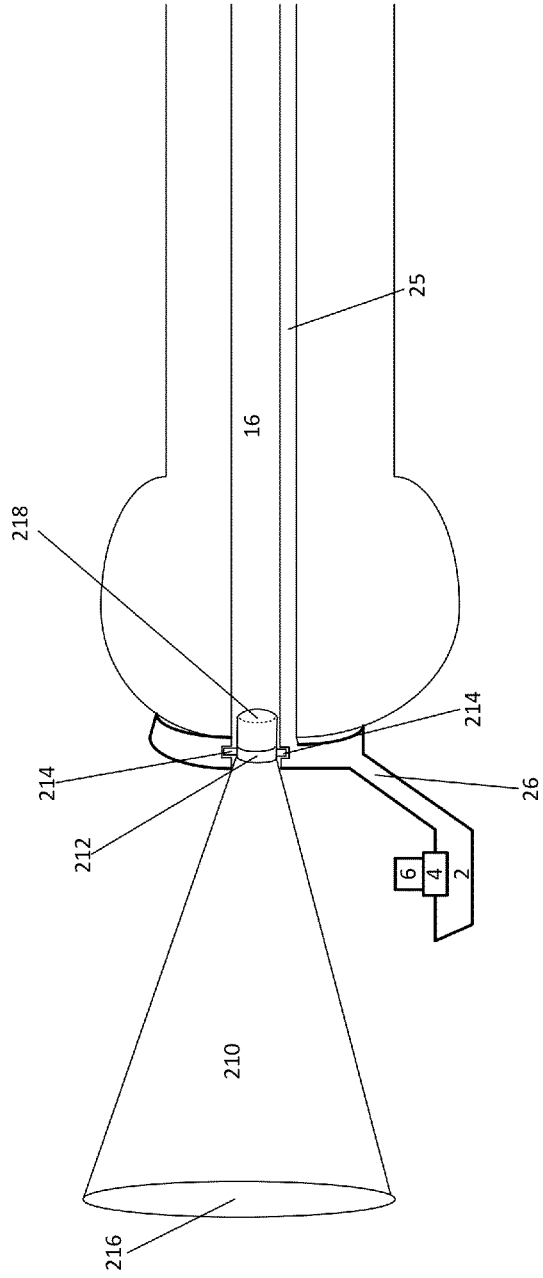
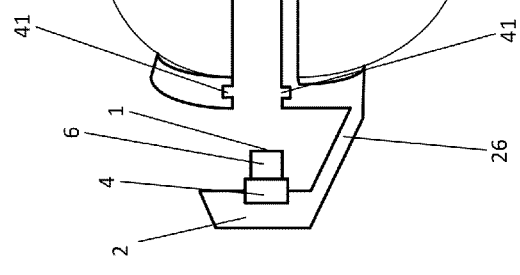
FIG. 20
FIG. 21

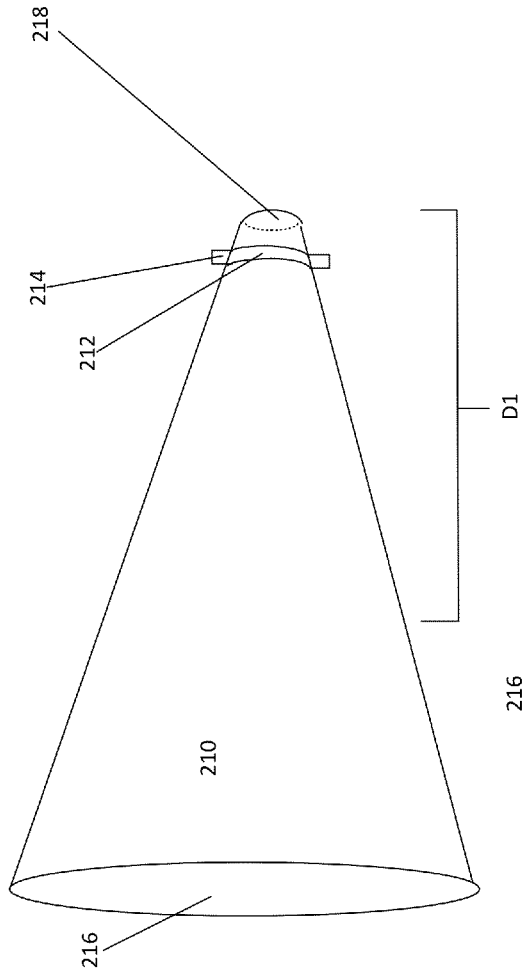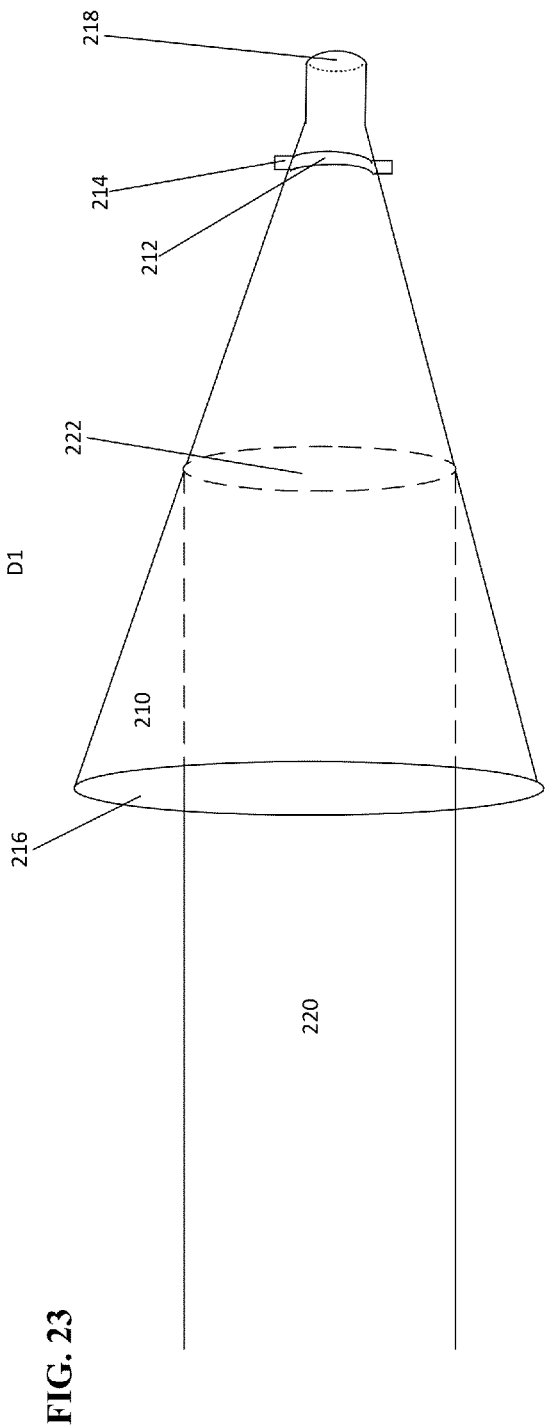
FIG. 22
FIG. 23

MEDICAL DEVICE FOR PROVIDING PORT-LIKE ACCESS TO A MAMMALIAN URINARY SYSTEM AND METHODS OF INSERTING AN UTILIZING THE SAME

CROSS-REFERENCE TO RELATED APPLICATION(S)

This application is a Continuation-in-Part of U.S. Ser. No. 13/594,523, filed on Aug. 24, 2012, now U.S. Pat. No. 8,870,852, titled A MEDICAL DEVICE FOR PROVIDING PORT-LIKE ACCESS TO A MAMMALIAN URINARY BLADDER AND METHODS OF INSERTING AND UTILIZING THE SAME, the disclosure of which is hereby incorporated by reference in its entirety.

TECHNICAL FIELD

The present disclosure relates generally to a medical device for providing direct port-like endoscopic access to the urinary system of a patient. More particularly, the medical device is low profile, designed for long term use and allows an operator to drain the urinary system or access the urinary system with minimal effort.

BACKGROUND

Access to the urinary bladder of a patient is sometimes necessary to treat a patient or to drain urine from the bladder of a patient. For example, in some instances the normal urinary flow of a patient may be blocked for one or more reasons. Some of these reasons include the swelling of the prostate (benign prostatic hypertrophy), congenital defects of the urinary tract, traumatic disruption of the urethra, obstructions such as kidney stones passed into the urethra, and cancer. When the normal urinary flow of the patient is obstructed a surgically-created connection between the urinary bladder and the skin, sometimes referred to as suprapubic cystostomy, is used to drain urine from the bladder. In a suprapubic cystostomy, medical personnel insert a catheter into the patient to allow urine to drain from the bladder. The catheters used in these procedures have several disadvantages, including their bulky size which leaves the patient with a large catheter protruding from the placement site. In some circumstances, medical personnel may place a Foley catheter into the patient's bladder via the urethra. This is uncomfortable for the patient and can easily become infected unless necessary precautions are taken, for example, drinking sufficient amounts of water, infrequently disconnecting the drainage bag and limiting sexual activity. As sexual activity of the elderly population increases the need to decrease or limit sexual activity in elderly patients has become an increasing concern.

Another instance where access to the urinary bladder of a patient is sometimes necessary is when medical personnel need to perform intra-bladder or intra-urethral procedures, for example, removing bladder stones, performing bladder biopsies, performing retrograde pyelograms, performing cystograms, and ureteral stent placement and removal. In these instances medical personnel often use a cystoscope or alternative devices to provide both visual and mechanical access to the immediate and surrounding procedure area via a patient's urethra. Each time access is necessary, a narrow tube is passed through the urethra into the bladder which allows medical personnel to use a light, camera, and tools to diagnose and treat bladder problems.

Like the use of a Foley catheter, this procedure is uncomfortable for the patient and requires repeating the entire process every time access is necessary.

SUMMARY

One aspect is a device for providing direct port-like endoscopic access to the bladder of a patient to assist the operator in performing intra-bladder or intra-urethral procedures, e.g., removing bladder stones, performing bladder biopsies, performing retrograde pyelograms, performing cystograms, ureteral stent placement and removal, flexible ureteroscopy, performing bladder instillations, bladder cycling and bladder training, mucous removal, and matrix stone removal.

In some embodiments, the device improves a patient's ability to drain their bladder. The device is easier to place and may be placed in an existing suprapubic tract by stage and/or primary placement. The device allows for easier exchange in the office rather than operating room after initial placement and may allow for patients to change at home, or be changed by nursing home staff or visiting nurses, thereby increasing physician availability for new patient visits and decreasing patient and insurance costs for repeat physician office procedural visits.

In some embodiments, the medical device is designed for and may be placed through the back of the patient so that the medical device terminates in the patient's kidney. Placement of the device between the patient's back and kidney allows medical personal to both drain fluid from the kidney and to have direct port-like access to the patient's kidney.

In other embodiments, the medical device is designed for and may be placed directly into the patient's urethra to become a low profile alternative to currently available products and to allow the patient to easily drain their bladder by simply opening the cap to the medical device.

In some embodiments, a medical device comprises a continuous hollow tube for spanning the distance between an exterior surface of a patient's suprapubic region and the patients urinary bladder having a diameter between 10 french and 40 french and a length between 0.8 cm and 15 cm. The hollow tube has an open proximal end and an open distal end, the proximal end of the hollow tube being longitudinally more rigid than the distal end.

The medical device may also comprise a first cap having a top surface and bottom surface that is operatively configured for securely attaching to the proximal end of the tube. The cap covers the open proximal end of the tube when securely attached to the proximal end of the tube and the bottom surface of the cap is recessed within the proximal end of the tube when securely attached.

The medical device may further comprise a hollow flexible stem fluidly connecting the cap and the proximal end of the hollow tube so that liquid may pass into the bottom surface of the cap, through the hollow flexible stem and into a separate channel within the hollow tube. The fluidly separate channel runs from the proximal end of the hollow tube toward the distal end of the hollow tube and the hollow flexible stem is permanently attached to the hollow tube below the open proximal end of the hollow tube.

The medical device may also comprise an inflation port on the bottom surface of the cap, the inflation port is operatively configured to receive liquid via a syringe so when the cap is not securely attached to the proximal end of the tube, liquid may be injected via the inflation port and travel from the cap, through the hollow flexible stem and down the separate channel within the hollow tube.

In some embodiments a medical device may comprise a second cap having a top surface and a bottom surface that is operatively configured to securely attach to the proximal end of the tube. The second cap may have at least one port from the top surface through to the bottom surface. In addition a medical device may comprise a one way valve located within the tube of the medical device to prevent liquid from traveling from the patient's urinary bladder to the proximal surface of the patient's suprapubic region when the first cap is not securely attached to the proximal end of the tube.

A variation of a medical device may comprise an inflatable balloon along the exterior surface (or partially interior surface) of the hollow tube and in fluid communication with the inflation port via the separate channel within the hollow tube.

In certain embodiments, a medical device of the present disclosure will sit substantially flush with the skin of the suprapubic region of the patient after insertion of the device into the patient. And in some embodiments the inflation port of the device sits at least partially beneath the skin of the suprapubic region of the patient after insertion of the device and when the cap is securely attached to the proximal end of the tube.

A medical device of the present disclosure, in some instances, will have a medial region located between the proximal end and the distal end of the hollow tube where the rigidity of the medial region is less than the proximal end and greater than the distal end.

In an embodiment of the present disclosure a method for inserting a medical device is disclosed, comprising the following steps: Inserting a needle from a patient's exterior surface of a suprapubic skin through to the patient's abdominal region and into the patient's urinary bladder to create a tract; threading a guide wire through the needle so the guide wire travels from the suprapubic skin of the patient into the urinary bladder of the patient; removing the needle while leaving the guide wire in the tract; dilating the tract to a desired width; measuring a distance between the patient's suprapubic skin and the patient's urinary bladder via the tract; and inserting a medical device suitable for use based on the previously measure distance.

A method for replacing a medical device is disclosed in the present disclosure, one embodiment comprising: placing a guide wire from a patient's suprapubic skin through the patient's abdominal region and into the patient's urinary bladder, the guide wire traveling from the suprapubic skin into the urinary bladder within a previously placed medical device; removing the previously placed medical device by sliding the device along the guide wire and away from the patient; filling the bladder of the patient; measuring a distance between the patient's suprapubic skin and the patient's urinary bladder; selecting a second medical device suitable for use based on the previously measure distance; inserting the selected medical device; and draining the urinary bladder of the patient.

Another aspect is a medical device comprising: a continuous hollow tube, the length sized for spanning the distance between an exterior surface of a mammal's back and the mammal's pelvis of its kidney, the hollow tube having an open proximal end and an open distal end; a first cap having a top surface and a bottom surface, the first cap being operatively configured for securely attaching to the proximal end of the tube; a hollow flexible stem fluidly connecting the first cap and the proximal end of the hollow tube so that liquid may pass into the bottom surface of the first cap, through the hollow flexible stem and into a separate channel within the hollow tube; and an inflation port on the bottom surface of the cap.

A further aspect is a medical device comprising: a continuous hollow tube, the length sized for spanning the distance between an exterior surface of a mammals skin and the mammal's pelvis of the kidney having a diameter between 10 french and 40 french, the hollow tube having an open proximal end and an open distal end; a first cap having a top surface and bottom surface that is operatively configured for securely attaching to the proximal end of the tube, the cap covering the open proximal end of the tube when securely attached to the proximal end of the tube, the bottom surface of the cap being recessed within the proximal end of the tube upon secure attachment; a hollow flexible stem fluidly connecting the cap and the proximal end of the hollow tube so that liquid may pass into the bottom surface of the cap, through the hollow flexible stem and into a separate channel within the hollow tube, the fluidly separate channel running from the proximal end of the hollow tube toward the distal end of the hollow tube, and the hollow flexible stem being permanently attached to the hollow tube below the open proximal end of the hollow tube; and an inflation port on the bottom surface of the cap, the inflation port being operatively configured to receive liquid via a syringe so when the cap is not securely attached to the proximal end of the tube liquid may be injected via the inflation port and travel from the cap, through the hollow flexible stem and down the separate channel within the hollow tube.

Yet another aspect is a medical device comprising: a continuous hollow tube, the length sized for spanning the distance between an exterior surface of a mammals skin and the mammal's bladder having a diameter between 10 french and 40 french, the hollow tube having an open proximal end and an open distal end; a first cap having a top surface and bottom surface that is operatively configured for securely attaching to the proximal end of the tube, the cap covering the open proximal end of the tube when securely attached to the proximal end of the tube, the bottom surface of the cap being recessed within the proximal end of the tube upon secure attachment; a hollow flexible stem fluidly connecting the cap and the proximal end of the hollow tube so that liquid may pass into the bottom surface of the cap, through the hollow flexible stem and into a separate channel within the hollow tube, the fluidly separate channel running from the proximal end of the hollow tube toward the distal end of the hollow tube, and the hollow flexible stem being permanently attached to the hollow tube below the open proximal end of the hollow tube; and an inflation port on the bottom surface of the cap, the inflation port being operatively configured to receive liquid via a syringe so when the cap is not securely attached to the proximal end of the tube liquid may be injected via the inflation port and travel from the cap, through the hollow flexible stem and down the separate channel within the hollow tube.

A further aspect is a universal connector comprising: a continuous hollow funnel shape having a larger opening at a first end and a smaller opening at a second end; an engagement apparatus adjacent to the second end; and protrusions operatively attached to the engagement apparatus so that when the second end of the universal connector is placed into a proximal end of a medical device the protrusions on the engagement apparatus can operatively engage with a locking mechanism on the proximal end of the medical device to permit fluid communication between the universal connector and the medical device.

Additional aspects are illustrated and described herein.

BRIEF DESCRIPTION OF DRAWINGS

FIG. 10b illustrates an embodiment of a second cap of the present disclosure having a larger single port within the cap than the embodiment in FIG. 10a.

FIG. 20 illustrates a close up view of FIG. 18 with the addition of an embodiment of the locking mechanism located at the proximal end of the medical device.

FIG. 21 illustrates a close up view of FIG. 18 with the addition of an embodiment of the locking mechanism located at the proximal end of the medical device and a universal adapter connected to the proximal end of the medical device via the locking mechanism.

FIG. 22 illustrates an alternative embodiment of a universal adapter.

FIG. 23 illustrates an embodiment of a universal adapter with an additional tube, e.g., drainage tube, inserted into the end of the universal adapter that does not connect to a medical device via a locking mechanism.

DETAILED DESCRIPTION

There is a need in the art for low-profile long-term device that allows port-like access to the urinary bladder or kidney of a patient without utilizing a patient's urethra. The device should allow a patient's bladder or kidney to drain as well as permit medical personnel access to the urinary bladder or kidney to diagnose and treat bladder or kidney problems. In addition, the low profile of the device should limit or decrease inadvertent removal of the device by confused patients, i.e., patients suffering from dementia, neural injury, trauma, medication or in the internal care unit. The present disclosure overcomes the shortcomings of the prior art and addresses these needs in the art.

There is also an additional need in the art for a low-profile long-term device that allows port-like access to the urinary bladder of a patient by utilizing a patient's urethra. The device should allow a patient's bladder to drain as well as permit medical personnel access to the urinary bladder to diagnose and treat bladder problems.

In addition, there is an additional need in the art for graduated measuring device to allow a physician to determine the distance between the patient's skin and kidney or urinary bladder thereby allowing the physician the ability to accurately select a device for insertion that will snugly fit the patient. Finally, there is a need in the art for universal connector that allows a large variety of medical tubing to fluidly and/or operatively connect to a medical device of the present disclosure.

Figure 1:
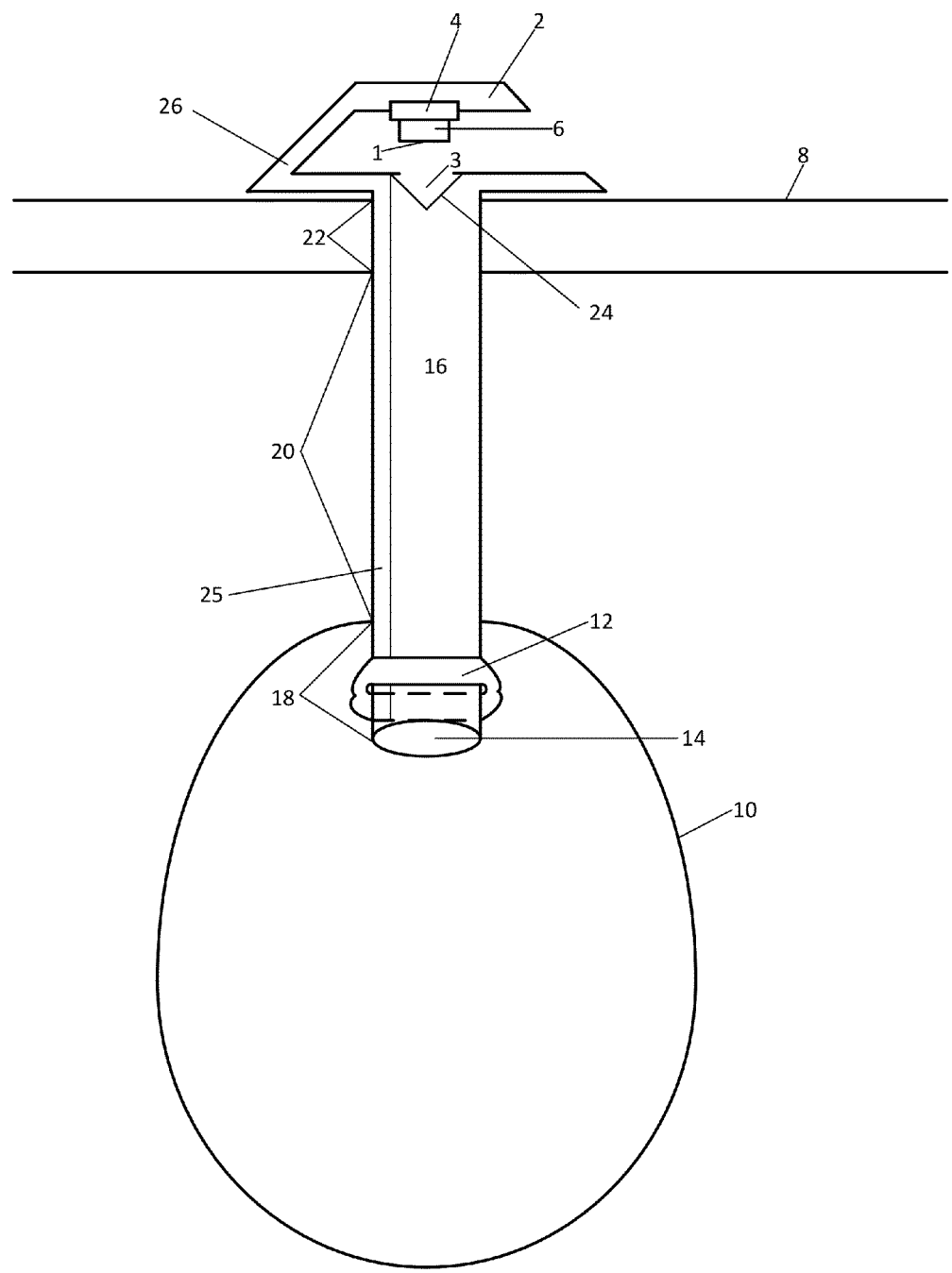
FIG. 1 illustrates a side profile of an embodiment of the medical device implanted in a patient with the first cap unsecured to the hollow tube.

Referring now to the drawings wherein like reference numerals designate identical or corresponding parts throughout the several views, an embodiment of medical device implanted in a patient with the first cap unsecured to the hollow tube is shown in FIG. 1. In an embodiment, a medical device has a continuous hollow tube 16 for spanning the distance between an exterior surface of a patient's suprapubic region 8 and the patient's urinary bladder 10 having a diameter between 10 french and 40 french and a length between 0.8 cm and 15 cm, the hollow tube having an open proximal end 3 and an open distal end 14, the proximal end 3 of the hollow tube 16 being longitudinally more rigid than the distal end 14. The first cap 2 having a top surface and bottom surface that is operatively configured for securely attaching to the proximal end 3 of the tube 16, the cap covering the open proximal end 3 of the tube 16 when securely attached to the proximal end 3 of the tube 16, the bottom surface of the cap 1 being recessed within the proximal end 3 of the tube 16 upon secure attachment.

A hollow flexible stem 26 fluidly connects the cap 2 and the proximal end 3 of the hollow tube 16 so that liquid may pass into the bottom surface of the cap 1, through the hollow flexible stem 26 and into a separate channel 25 within the hollow tube 16. The fluidly separate channel 25 runs from the proximal end 3 of the hollow tube 16 toward the distal end 14 of the hollow tube 16, and the hollow flexible stem 26 is permanently attached to the hollow tube 16 below the open proximal end 3 of the hollow tube 16.

The medical device may further comprise an inflation port 6 on the bottom surface of the cap 2. The inflation port 6 is operatively configured to receive liquid via a syringe 29 so when the cap 2 is not securely attached to the proximal end 3 of the tube 16 liquid may be injected via the inflation port 6 and travel from the cap 2, through the hollow flexible stem 26 and down the separate channel 25 within the hollow tube 16.

In some embodiments, the diameter of the hollow tube 16 is between 10 french and 50 french (6 Fr-50 Fr). However, in additional embodiments the diameter of the hollow tube may change depending on the patient's needs and the medical personnel's preferences. For example, the medical personnel may require a larger diameter to permit the use of multiple or different instruments depending on the anticipated medical procedure. In another example the size of the patient may dictate the diameter of the hollow tube, i.e., a patient with a larger suprapubic region 8 mass or distance between the suprapubic region 8 and bladder 10 may require a larger diameter tube 16.

In certain embodiments the diameter of the tube 16 will be between 15 french and 35 french, between 20 french and 30 french, between 10 french and 30 french, between 10 french and 20 french, between 20 french and 40 french or between 30 french and 40 french.

In some embodiments the diameter of the tube will be greater than 10 french, greater than 20 french, greater than 30 french or greater than 40 french. In other embodiments the diameter of the tube will be less than 50 french, less than 40 french, less than 30 french or less than 20 french.

It will be appreciated that in some embodiments the tube 16 has a substantially continuous diameter from the proximal end 3 to the distal end 14. However, in some embodiments the diameter of the tube 16 may change. For example, the proximal region 22 of the tube may be one diameter, while the distal region 18 of the tube 16 is a similar or different diameter and the medial region 20 of the tube is a similar or different diameter. The difference in diameters may be important to helping control how rigid the tube 16 is or helping to prevent the medical device from accidently coming out. In some embodiments the diameter of the tube 16 will gradually increase or decrease from the proximal end 3 to the distal end 14.

In some embodiments, the length of the hollow tube 16 is between 0.8 cm and 40 cm. However, in additional embodiments the length of the hollow tube may change depending on the patient's needs and the medical personnel's preferences. For example the size of the patient may the length of the hollow tube, i.e., a patient with a larger suprapubic region 8 mass or distance between the suprapubic region 8 and bladder 10 may require a longer tube 16.

In certain embodiments the length of the tube 16 will be between 5 cm and 25 cm, between 10 cm and 20 cm, between 0.8 cm and 20 cm, between 0.8 cm and 10 cm, between 5 cm and 30 cm, between 10 cm and 30 cm, between 15 cm and 30 cm or between 20 cm and 30 cm.

In some embodiments the length of the tube 16 will be greater than 3 cm, greater than 8 cm, greater than 12 cm, greater than 18 cm, greater than 22 cm or greater than 26 cm. In other embodiments the length of the tube 16 will be less than 30 cm, less than 25 cm, less than 20 cm, less than 15 cm, less than 10 cm or less than 5 cm.

Figure 16:
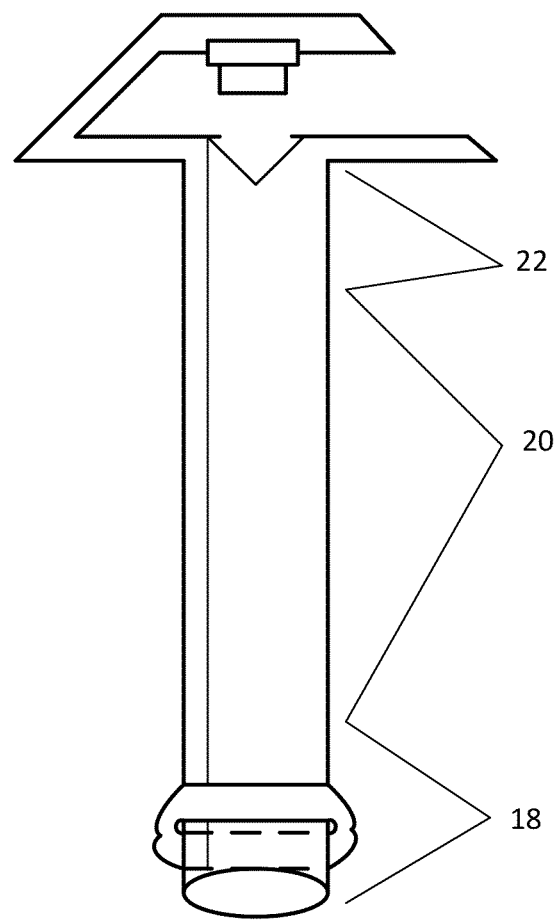
FIG. 16 illustrates an embodiment where the hollow tube of the medical device has three different regions of longitudinal rigidity.

Still referring to FIG. 1 (see also FIG. 16), in some embodiments the proximal end 3 of the hollow tube 16 is longitudinally more rigid than the distal end 14. In other embodiments, proximal end 3 of the hollow tube 16 is longitudinally less rigid than the distal end 14. The difference in rigidity may be important to improving comfort to a patient, e.g., less rigid within the proximal region 22, or providing attributes to enhance a medical personnel's ability to manipulate instruments through the tube, e.g., more rigid in the distal region 18. In certain embodiments the entire tube 16 will have the same rigidity or flexibility. However, in other embodiments the rigidity may differ between the distal 14 and proximal 3 ends or the distal 18 and proximal regions 22 of the tube 16. In some embodiments the tube may comprise three regions, a proximal region 22, a medial region 20 and a distal region 18. Each region may have a different rigidity or similar rigidity.

In certain embodiments the rigidity of the one region to another region, or proximal end 3 to distal end 14 (and vice versa), may be at least 1.0 time more rigid, at least 1.5 times more rigid, at least 2.0 times more rigid, at least 2.5 times more rigid, or at least 3.0 times for rigid. In additional embodiments the difference in rigidity between regions on the hollow tube may be between 1.0 and 10 times, between 2.0 and 8.0 times, or between 3.0 and 6.0 times.

Still referring to FIG. 1, the tube 16, and sometimes the entire device is made from silicone or latex, although any biocompatible material is suitable. In a preferred embodiment the tube or the device is substantially clear.

Still referring to FIG. 1, the first cap 2 is operatively configured for securely attaching to the proximal end 3 of the tube 16. The secure attachment may occur through a variety of suitable arrangements, including typical male-female connections. In an embodiment the first cap 2 snaps into the opening in the proximal end 3 of the tube 16 (e.g., FIG. 2). In all methods of secure attachment once the first cap is securely attached to the proximal end, the proximal end is no longer open and a force is required to disengage the first cap 2 from the proximal end 3.

Figure 2:
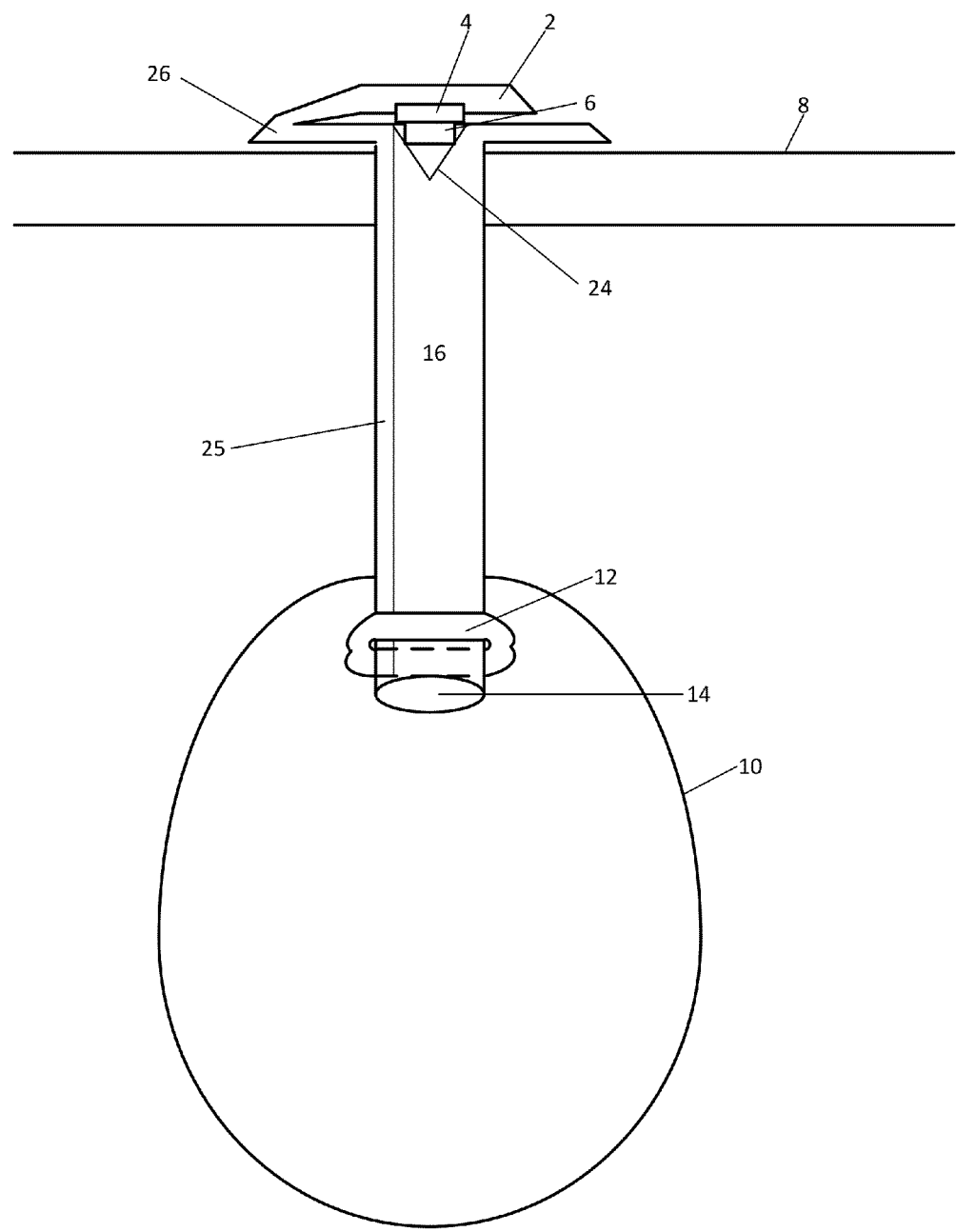
FIG. 2 illustrates a side profile of an embodiment of the medical device implanted in a patient with the first cap secured to the hollow tube.
Figure 4:
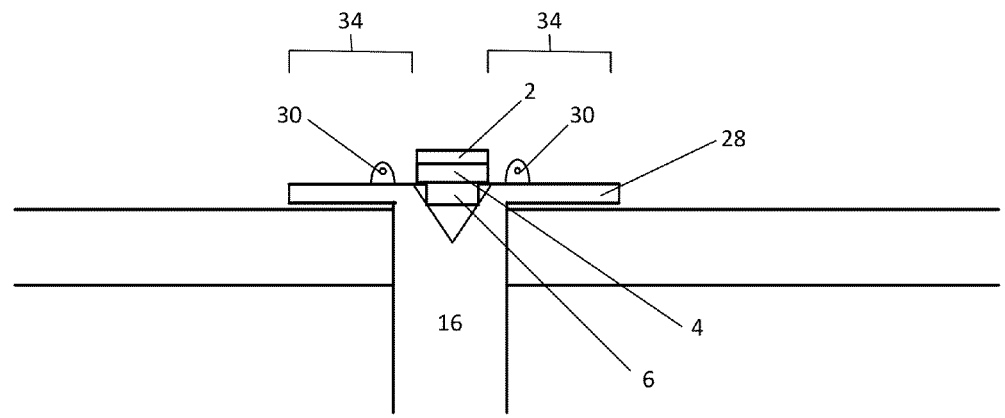
FIG. 4 illustrates an alternative side profile, rotated 90 degrees from FIG. 1-3, of an embodiment of the medical device with an emphasis on the proximal end of the medical device.

When the first cap 2 is securely attached to the proximal end 3 of the tube 16, the inflation port 6 and inflation port valve 4 are recessed within the proximal end 3 of the hollow tube 16, e.g., FIGS. 2 and 4. This configuration allows the medical device to have a lower and smaller profile upon insertion to the patient, e.g., the amount of the device that protrudes above the patient's suprapubic skin 8 is reduced by allowing the inflation port 6 and inflation port valve 4 to recess within the hollow tube 16.

In an embodiment the inflation port 6, the inflation port valve 4, the hollow flexible stem 26 and the separate channel 25 are in fluid communication and isolated from any fluid that may flow between the patient's skin surface at the suprapubic region 8 and the patient's bladder 10 via the tube 16.

The inflation port 6 on the bottom surface of the cap 2 is capable of receiving liquid via a syringe 29 or equivalent device. In some embodiments, the inflation port 6 has a built in one way valve to prevent liquid from accidently or inadvertently flowing out the inflation port 6 without operator manipulation. In other embodiments, an inflation port valve 4 is also present and performs substantially the same function, i.e., prevent liquid from accidently or inadvertently flowing out the inflation port 6 without operator manipulation.

In some embodiments, the medical device further comprises an inflatable balloon-like component 12 that is fluidly connected to the separate channel 25 and capable of receiving air or liquid via the inflation port 6. The balloon like component 12 is affixed to the tube 16 prior to insertion of the medical device into a patient. The balloon-like component 12 may be affixed to the tube 16 in a variety of fashions including affixation to the exterior surface of the tube 16, the interior surface of the tube 16, directly to the separate channel 25, or some combination thereof. In all embodiments the balloon-like component is in fluid communication with the separate channel 25 and fluidly isolated from the tube 16 or patient's bladder 10.

Figure 3:
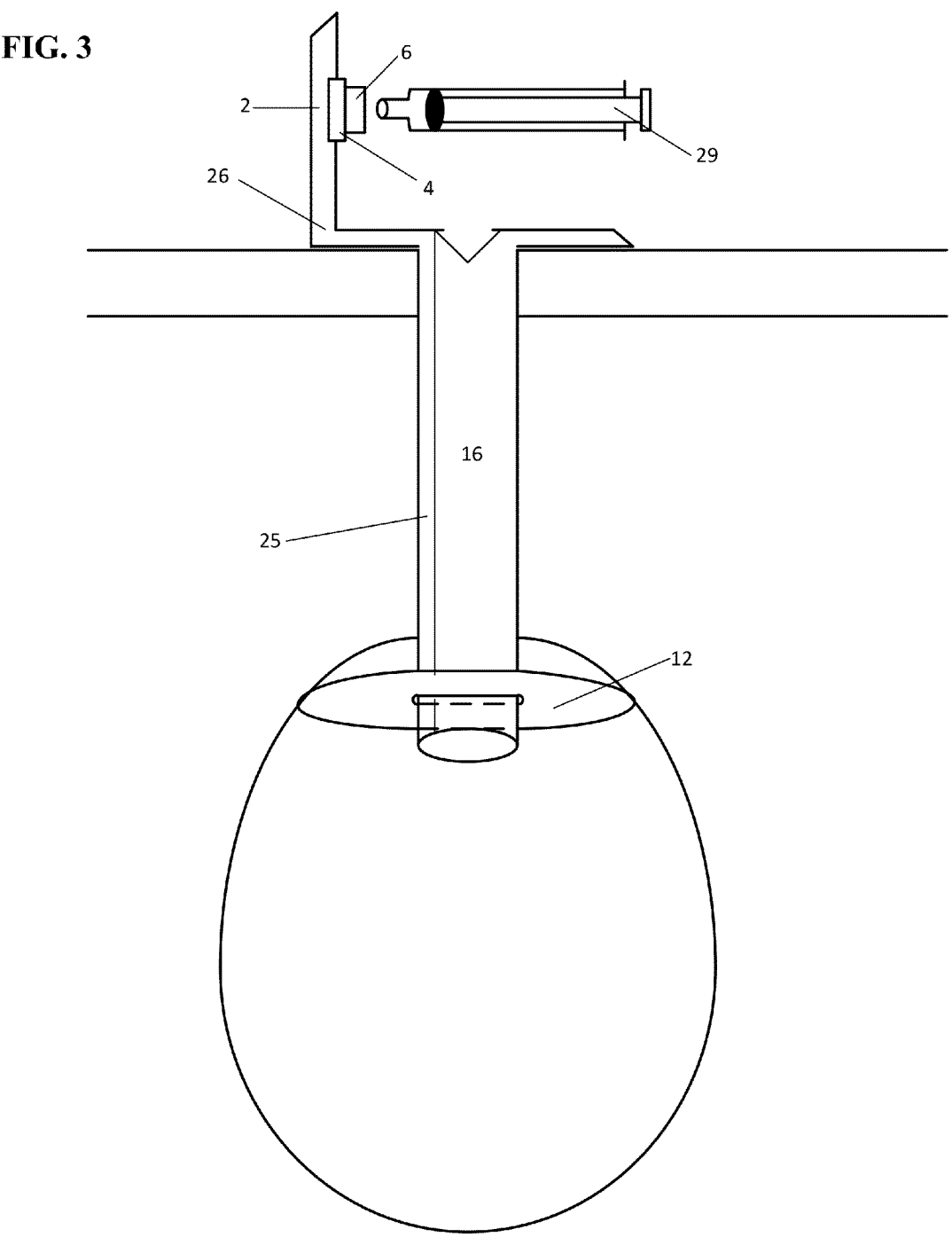
FIG. 3 illustrates a side profile of an embodiment of the medical device implanted in a patient with the first cap unsecured to the hollow tube and a syringe.

When the medical device is inserted into a patient the balloon-like component 12 is substantially empty of water or air, i.e., deflated as shown in FIG. 1. Following insertion of the medical device, the balloon-like component 12 is inflated using liquid or air via the inflation port 6 as shown in FIG. 3. Upon inflation, the balloon-like component rests against the bladder wall to help hold the medical device in place and prevent the medical device from backing out of the patient. In some instances, the inflated balloon-like component will act as a plug to help prevent liquid from inadvertently leaking from the bladder via the channel in the patient's suprapubic region, i.e., not via the medical device. In a preferred embodiment, the balloon-like component has a donut-like shape when inflated as opposed to a more basketball-like shape. When it is necessary to remove the medical device, liquid or air is removed from the balloon-like component via the inflation port 6. Removal of the liquid or air deflates the balloon-like component 12, allowing removal of the medical device.

In some embodiments, the balloon-like component 12 is substantially flush with the distal end 14 of the tube 16 after inflation. In other embodiments the balloon-like component 12 is recessed from the distal end 14 of the tube 16 after inflation, i.e., the balloon-like component is a small distance toward the proximal end 3 of the tube thereby leaving a gap between the distal end 14 of the tube and the inflated balloon-like component 12. The placement of the balloon-like component 12 at a flush or recessed position with the distal end 14 prevents medical instruments from contacting and possibly puncturing the balloon-like component during procedures. In addition, the location of the balloon-like component prevents it from interfering with the flow of fluids, i.e., urine, between the surface of the patient's skin and the patient's bladder via the tube 16.

Referring to FIG. 1, in some embodiments the proximal end 3 of the tube 16 may further comprise a one way valve 24 located within the tube 16 of the medical device to prevent liquid from traveling from the patient's urinary bladder to the proximal surface of the patient's suprapubic region without additional manipulation. In an embodiment the one way valve 24 prevents the flow of liquid irrespective of whether the first cap 2 is securely configured to the proximal end 3 of the tube 16. Therefore, in an embodiment the one way valve 24 prevents liquid from escaping the bladder when the first cap is not securely attached to the proximal end of the tube. In some embodiments the one way valve 24 allows liquid, e.g., urine, to travel from the bladder upon manipulation by medical personnel or patient, for example, following the attachment of a catheter drainage tube to the proximal end of the medical device.

In some embodiments the one way valve is flexible, e.g., rubber or latex, and allows the insertion of medical instruments through the tube into a patient's bladder without breaking or substantially altering the purpose of the one way valve 24.

Figure 5:
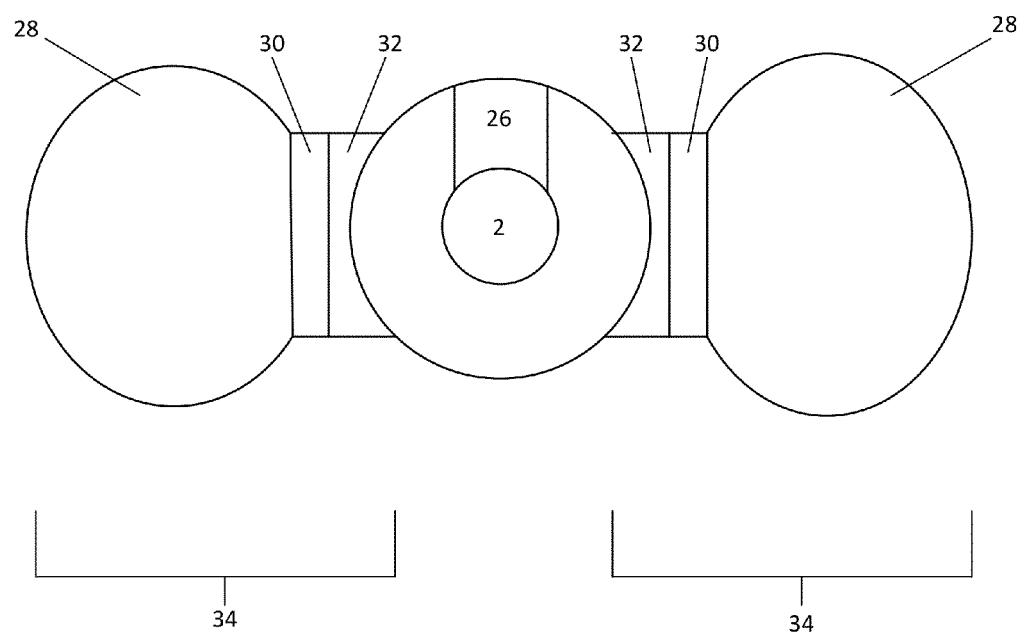
FIG. 5 illustrates a top view of an embodiment of the medical device.

Referring now to FIG. 4 and FIG. 5 which disclose an alternative side profile (FIG. 4) or top profile (FIG. 5), rotated 90 degrees from FIG. 1-3, of embodiments of the medical device with an emphasis on the proximal end of the medical device. In FIG. 4, the first cap 2 along with an inflation port 6 and inflation port valve 4 are securely attached to the proximal end of the tube 16. The flexible stem is not shown in FIG. 4 as it is hidden behind the first cap 2. Shown in FIG. 4 is an embodiment of the medical device that includes suture anchors 30 for suturing the medical device to the patient's skin after insertion of the device. The suture anchors 30 are located within the retention wings 34 that span out from the proximal end 3 of the tube 16. As shown in FIG. 4, the suture anchors are hollow holes within a raised portion of the retention wings 34 that allow a medical operator to thread a suture through the holes and into a patient's skin. While hollow holes are shown in FIG. 4, the suture anchors 30 may take on any number of configurations suitable for helping maintain the placement of the suture, e.g., indentations in the surface of the retention wings 34 or raised bevels on the surface of the retention wings 34. There may be a single suture anchor 30 or a plurality of suture anchors 30.

The retention wings 34 protrude outward from the first cap 2 as shown in top view of the medical device with a first cap 2 securely attached to the proximal end of the tube 16 in FIG. 5. As shown in FIG. 4 the retention wings 34 have a low profile and sit adjacent to a patient's skin following insertion of the medical device. As shown in FIG. 5 the retention wing ends 28 are a circular shape; however, the retention wing ends 28 may take on any shape. In one embodiment, the retention wing ends 28 are wider than the suture anchors 30 to help stabilize the sutures. The retention wings 34 not only provide a platform for the suture anchors 30 but also provide a surface area to oppose the balloon-like component 12 following inflation. This opposition stabilizes the placement of the medical device and prevents the medical device from inadvertently being pushed farther into the patient or pulled out of the patient.

Figure 8:
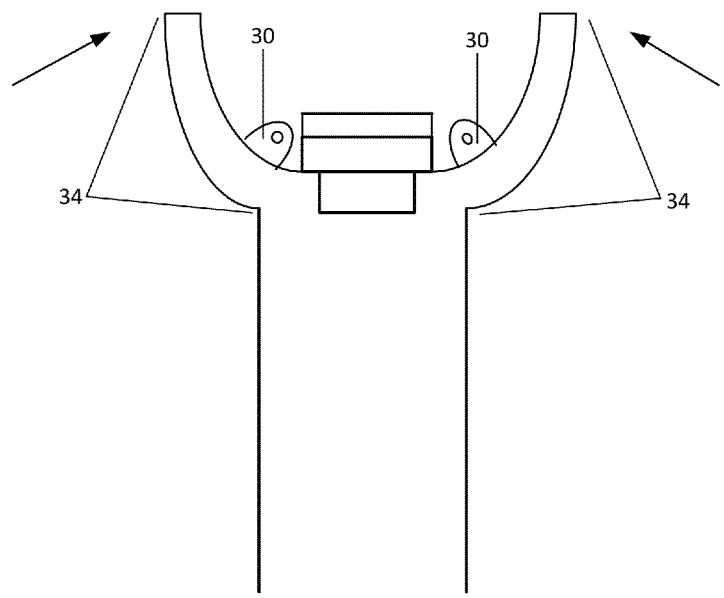
FIG. 8 illustrates a side profile, 90 degrees from FIG. 1-3, of an embodiment of the medical device with an emphasis on the flexibility of the wings at the proximal end of the medical device.

Referring now to FIG. 8, the retention wings 34 are elastic and flexible in some embodiments. In these embodiments medical personnel or a patient may use the retention wings 34 to grip the medical device during insertion or removal by using an opposing finger and thumb to push inward and upward (as indicated by the arrows). The flexibility of the retention wings 34 provides better grip and control over the device during placement and removal.

Figure 6:
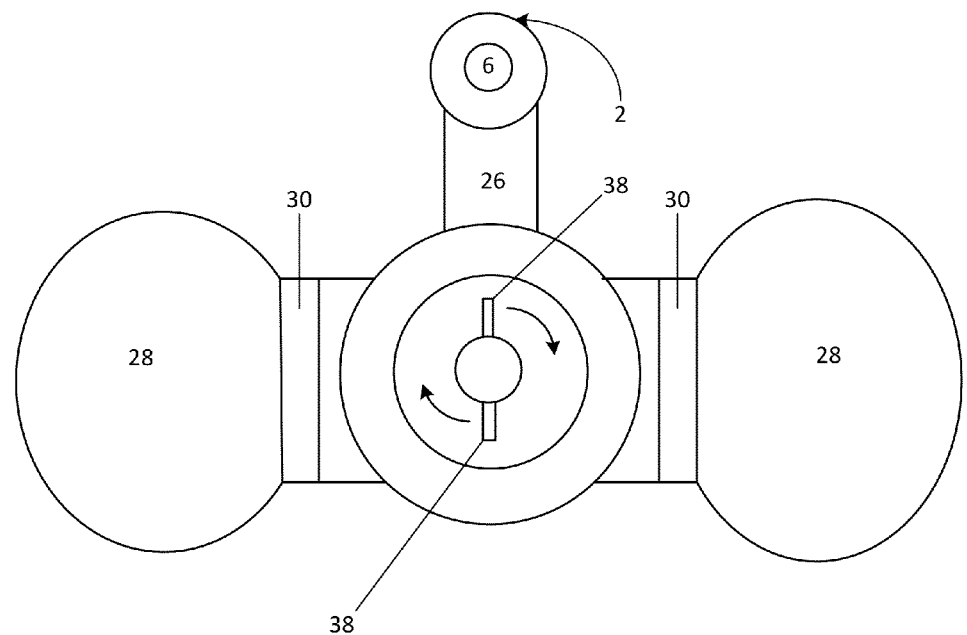
FIG. 6 illustrates a top view of an embodiment of the medical device with an emphasis on one embodiment of the valve and locking mechanism located at the proximal end of the medical device.
Figure 7:
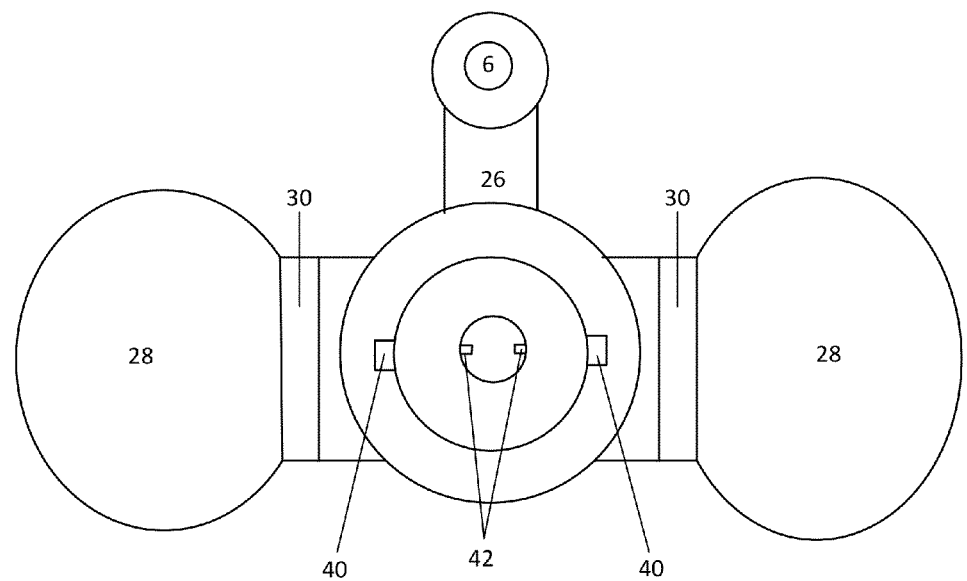
FIG. 7 illustrates a top view of an embodiment of the medical device with an emphasis on an alternative embodiment of the valve and locking mechanism located at the proximal end of the medical device.

Some embodiments of the medical device will comprise a locking mechanism at the proximal end 3 of the tube 16, e.g., as shown in FIG. 6 and FIG. 7. FIG. 6 and FIG. 7 are both a top view of an embodiment of the medical device when the first cap 2 with inflation port 6 are not securely attached to the proximal end 3 of the tube 16, e.g., the first cap 2 is in an open configuration and the viewer is looking directly down the tube 16. The locking mechanism is used to attach external devices, e.g., drainage tubing, to the proximal end of the medical device. For example, when a patient or medical personnel desires to drain the bladder of the patient, they may open the cap 2, and attached a drainage tube to the proximal end 3 of the tube 16 so that the drainage tube and tube are in fluid communication via the locking mechanism. The locking mechanism holds the drainage tube in place and allows liquid to flow freely from the patient's bladder to a source outside the patient's body. It is important to note that the presence of the locking mechanism does not prevent instrument access to a patient's bladder via the tube 16 when a drainage tube is not attached to the tube 16.

In some embodiments, the medical device further includes catheter tubing, e.g., drainage tube, that is manufactured and sold with at least one end of the tubing configured to operatively connect to a specific locking mechanism on the proximal end 3 of the tube 16. In some embodiments, when the medical device has a locking mechanism, the medical device also comes with a separate corresponding mate to the locking mechanism that can connect (plug into an open end of the tubing or clamp around an open end of the tubing) to standard catheter tubing thereby allowing the standard catheter tubing to operatively connect to the locking mechanism of the medical device.

FIG. 6 shows an embodiment of the present disclosure with a twist locking mechanism 38 that allows the connection of external devices via the twist lock 38. This locking mechanism, usually made of plastic, has key holes that match the external drainage tubing teeth. Once the external drainage tubing with teeth are placed into position, the patient or medical personnel placing the tubing just twists the drainage tubing teeth to the right and the drainage tubing teeth lock into place. Once drainage is finished, a simple twist in the opposite direction moves the teeth back into the keyhole tracts and one lifts the tubing out.

FIG. 7 shows an embodiment of the present disclosure with a push-button locking mechanism. This locking mechanism (usually made of plastic) has two sets of teeth or pins 40 and 42 that when in an untouched or natural state are plunged toward the center of the tube. When medical personnel or patient wants to insert a drainage tube, the teeth or pins 40 and 42 are pinched open by applying pressure to the opposite ends of the tube 16 to allow placement of the drainage tubing. Once the tubing is in place, the pressure is released and the teeth or pins 40 and 42 settle in and lock over a ridge on the drainage tubing. In some embodiments, no locking mechanism is necessary or alternative mechanisms for connecting external tubing or instruments are employed.

Figure 9A:
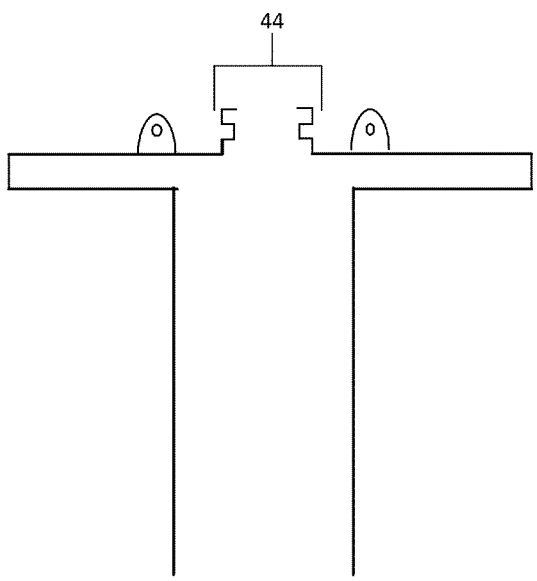
FIG. 9a illustrates a side profile, 90 degrees from FIG. 1-3, of an embodiment of the medical device with an emphasis on the configuration for receiving a second cap.
Figure 9B:
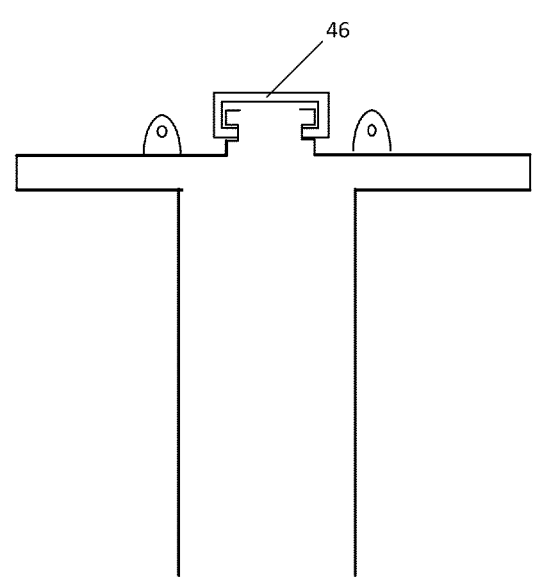
FIG. 9b illustrates a side profile, 90 degrees from FIG. 1-3, of an embodiment of the medical device with an emphasis on the configuration for receiving a second cap.
Figure 10C:
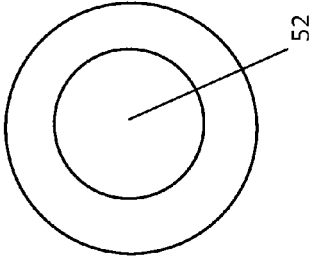
FIG. 10c illustrates an embodiment of a second cap of the present disclosure having a larger single port within the cap than the embodiment in FIG. 10a or FIG. 10b.
Figure 10B:
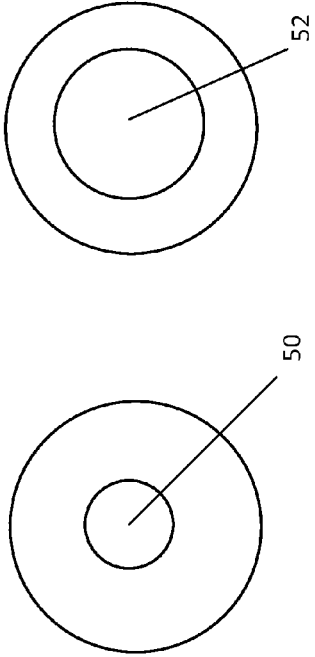
Figure 10A:
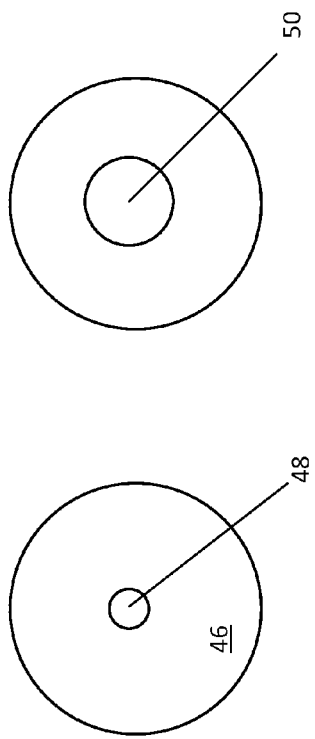
FIG. 10a illustrates an embodiment of a second cap of the present disclosure having a single port within the cap.
Figure 10F:
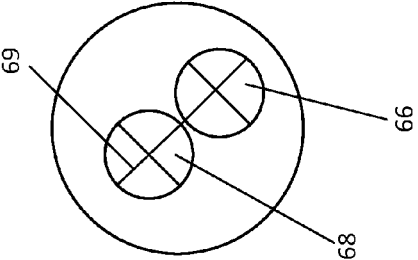
FIG. 10f illustrates an embodiment of a second cap of the present disclosure having two ports within the cap.
Figure 10E:
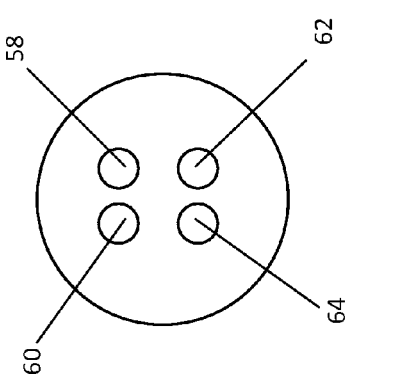
FIG. 10e illustrates an embodiment of a second cap of the present disclosure having four ports within the cap.
Figure 10D:
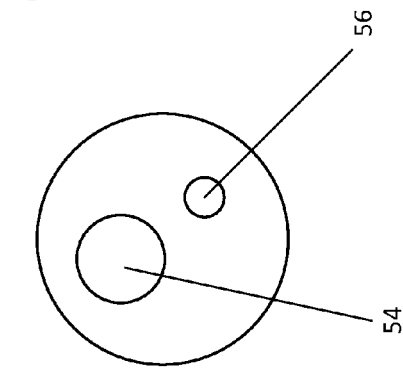
FIG. 10d illustrates an embodiment of a second cap of the present disclosure having two ports within the cap, one larger and one smaller.

Referring now to FIGS. 9a and 9b, some embodiments of the present disclosure comprise a ridge 44 at the proximal end of the tube 16. The ridge sits above the surface of the retention wings 34 and does not interfere with the ability of the first cap 2 to securely attach to the proximal end of the tube 16. In some embodiments the attachment of the first cap 2 to the proximal end of the tube is via the ridge 44. The ridge 44 is operatively configured to accept a second cap 46 via a thread mechanism, a snap mechanism or similar removable but secure attachment. A second cap 46 is independent of the medical device and is not permanently attached to the medical device. Medical personnel may screw or snap a second cap 46 into place via the ridge 44 when the first cap 2 is in the open position, e.g., FIG. 3.

A second cap 46 may be solid, i.e., have not holes or may include a variety of ports 48-66 as shown in FIG. 10a-10f. The ports may take on a circular shape or any other shape and size, and may be placed at distinct positions within a second cap. In an embodiment a second cap has two circular ports (FIG. 10f) and is placed over the open proximal end of a tube via the ridge 44. In an embodiment each port has a rubber cover that may be penetrated by an instrument medical personnel may place into the patient's bladder via the medical device. In some embodiments the rubber covers have flexible slits 69 that enhance penetration by a medical instrument.

In an embodiment medical personnel may remove the first cap 2 and place a second cap 46 with two ports 66 and 68 onto the medical device via the ridge 44. The medical personnel will then access the patient's bladder for purposes of treatment or diagnosis with instruments via the two ports 66 and 68. One advantage of using a second cap 46 with ports is to decrease the size of the opening directly into the patient's bladder via the medical device and minimize the chance of infection.

A major advantage to the medical device of the present disclosure is that is minimizes the amount of the device protruding from a patient's suprapubic region by putting the inflation port 6 into the first cap 2 of the device. This is a huge advantage over current devices because it less likely to become inadvertently removed, decreases the chances for infection and increases patient comfort. This leads to increased patient confidence and the likelihood a patient will comply with treatment. In some embodiments, the proximal end 3 of the device with first cap 2 and retention wings 34 sits substantially flush with the skin of the patient after insertion of the device. In an embodiment the top of the medical device after insertion into a patient is less than 1 inch from the patient's skin, less than 0.75 inches from the patient's skin, less than 0.5 inches from the patient's skin, less than 0.4 inches from the patient's skin, is less than 0.3 inches from the patient's skin, is less than 0.2 inches from the patient's skin, is less than 0.1 inches from the patient's skin.

In an embodiment, the inflation port of the medical device is at least partially beneath the skin of the suprapubic region of the patient after insertion of the device and when the cap is securely attached to the proximal end of the tube.

Figure 11:
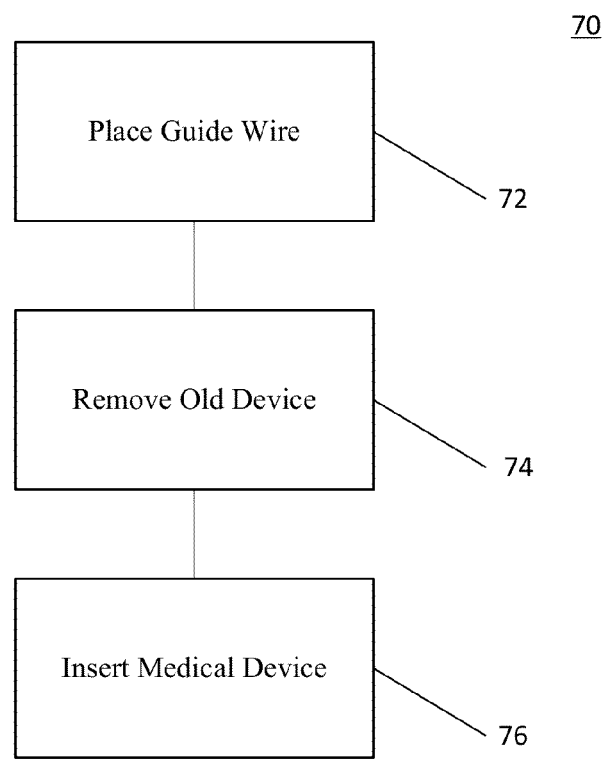
FIG. 11 illustrates steps medical personnel may take for replacing an old medical device with a new medical device of the present disclosure.

Referring now to FIG. 11 where an example method 70 for replacing an old medical device spanning the suprapubic region and urinary bladder of a patient with a device of the present disclosure is described. First, medical personnel insert a guide wire into the hollow channel of the old device 72. The old device is then removed by slipping it over the guide wire and leaving the guide wire in place, i.e., spanning the distance between the patient's suprapubic region and urinary bladder 74. A device of the present disclosure is then inserted over the guide wire and into position 76.

Figure 12:
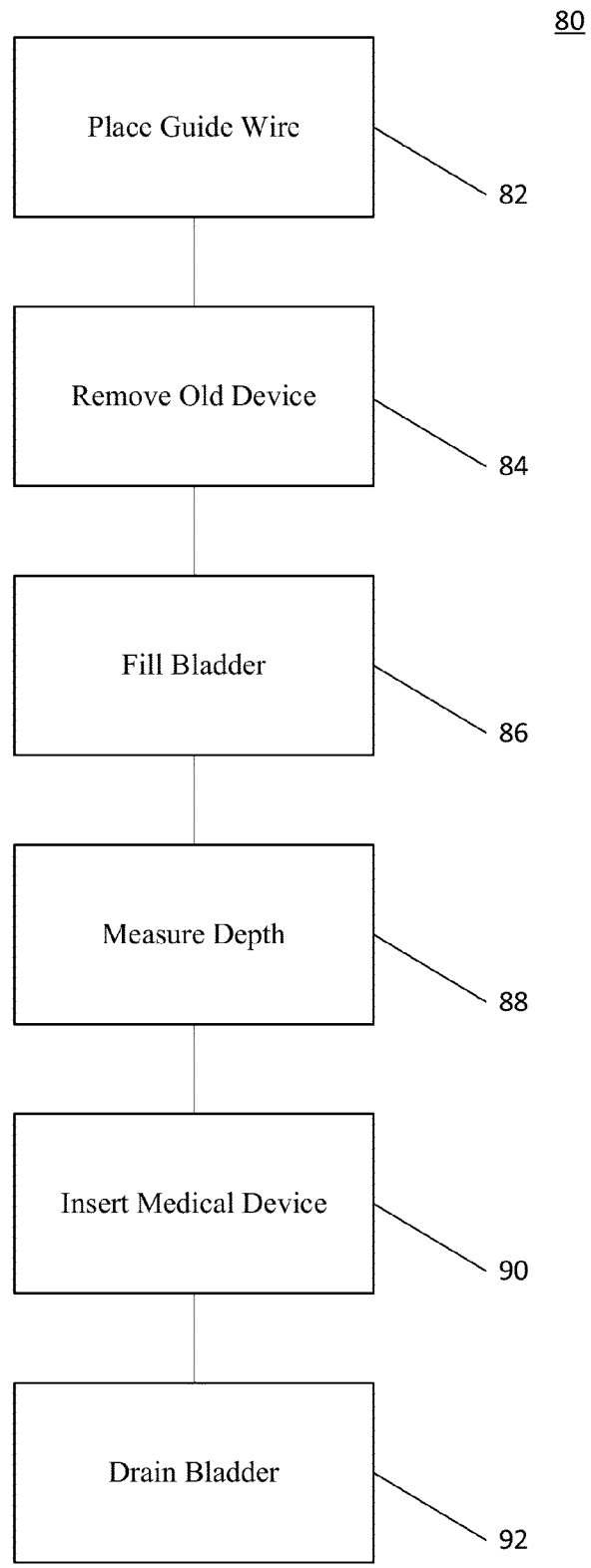
FIG. 12 illustrates steps medical personnel may take for replacing an old medical device with a new medical device of the present disclosure.

FIG. 12 discloses an additional method 80 of the present disclosure. First medical personnel insert a guide wire into the hollow channel of the old device 82. The old device is then removed by slipping it over the guide wire and leaving the guide wire in place, i.e., spanning the distance between the patient's suprapubic region and urinary bladder 84. The bladder of the patient if then filled with liquid to expand the patient's bladder 86. The distance between wall of the patient's bladder and the surface of the patient's suprapubic region is measured, e.g., using a depth gauge, i.e., graduate measuring device 88. Measuring the distance allows the medical personnel to choose a medical device of the present disclosure with the best length for fitting the patient. In an embodiment the depth gauge is designed much like a council tip catheter with a drainage attachment area and balloon inflation port at one end, which allow for access of a guide wire during placement and balloon inflation and deflation while determining the depth of device necessary for patient body size. The depth gauge can be clear and have black hash marks on the side measuring the distances from just above the balloon to almost the drainage tip. There is a moveable surface lock that rests on the skin edge, where the depth gauge disc will rest, and will define the depth of the device needed, by looking at the hash mark that it relates to. The internal end of the depth gauge has a balloon for inflation and to hold depth gauge in place while measuring, and has a council tip that allows for the guide wire to pass through centrally.

Figure 13:
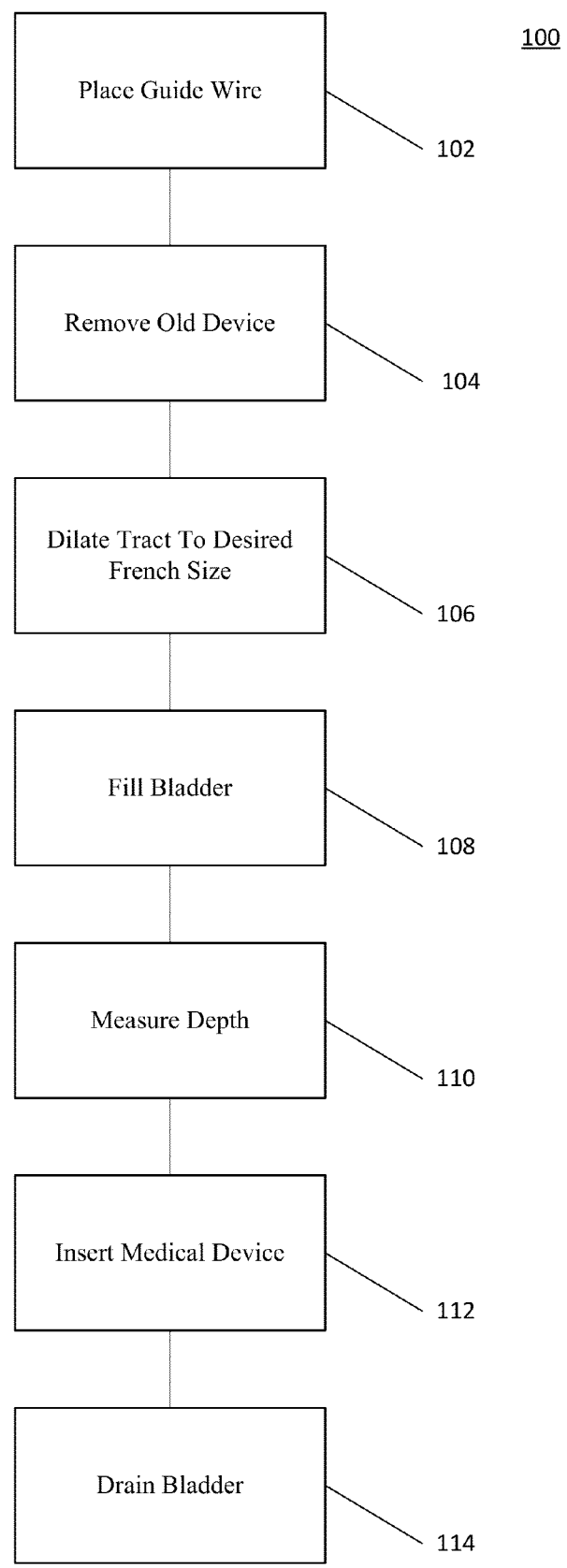
FIG. 13 illustrates steps medical personnel may take for replacing an old medical device with a new medical device of the present disclosure.

Still referring to FIG. 12, after determining to the depth of the previously established tract, a properly sized medical device of the present disclosure is inserted into the patient over the guide wire 90. The patient's bladder is then drained 92. In some embodiments, e.g., FIG. 13, a larger tract may be necessary then the tract previously established by the old medical device. In this situation, medical personnel may dilate the existing tract to a desire french size 106 in between removing the old device 104 and inserting the new device 112.

Figure 14:
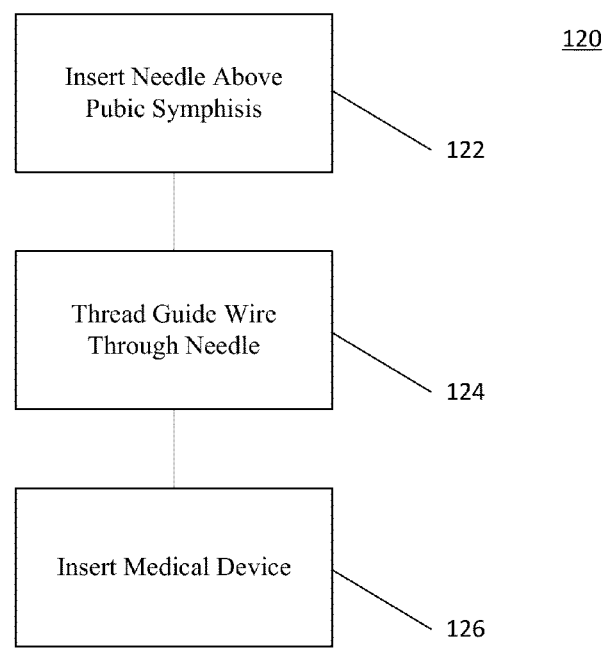
FIG. 14 illustrates steps medical personnel may take for inserting a new medical device of the present disclosure where a tract did not previously exist.

Referring now to FIG. 14 where a method 120 for inserting device by creating a new tract between a patient's suprapubic region and urinary bladder is disclosed 120. First medical personnel will insert a needle above the patient's pubic symphisis into the patient's urinary bladder 122. A guide wire is then threaded through the needle 124. The needle is removed and a medical device is inserted into the tract created by the needle and over the guide wire 126.

Figure 15:
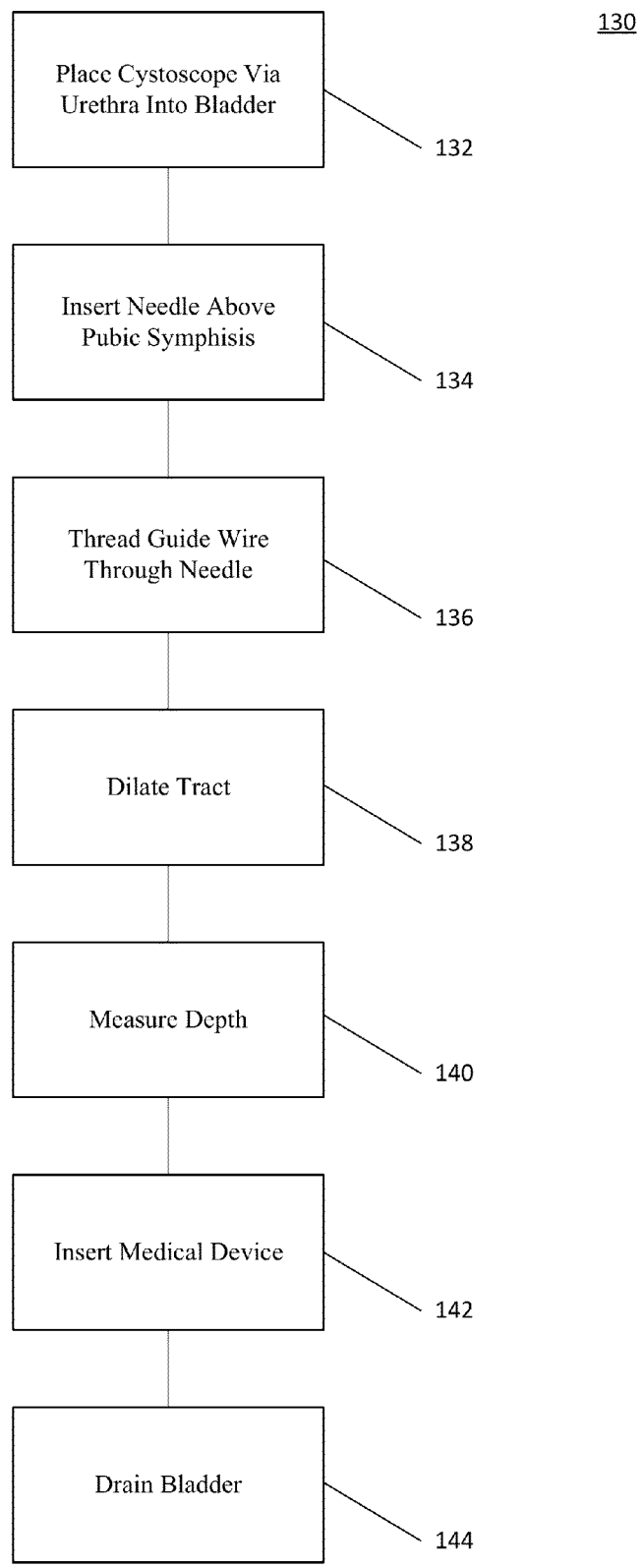
FIG. 15 illustrates steps medical personnel may take for inserting a new medical device of the present disclosure where a tract did not previously exist.

FIG. 15 discloses an additional method 130 for inserting a device by creating a new tract between a patient's suprapubic region and urinary bladder. To aid the medical personnel in creating new tract a cystoscope is placed into the patient's bladder via the patient's urethra 132. Medical personnel will insert a needle above the patient's pubic symphisis into the patient's urinary bladder 134 under observation of the cystoscope. A guide wire is threaded through the needle 136 and the needle is removed. The tract created by the needle and occupied by the guide wire is dilated to a desired french size 138. The depth of the tract is measured 140 using a depth gauge as previously described 88 and in some embodiments the bladder may be filled with liquid prior to measuring the depth. The device is selected based on the measured depth and inserted into the patient over the guide wire through the newly formed tract 142. In some embodiments the patient's bladder is then drained if it was full or had been filled earlier in the procedure 144.

A method for inserting a medical device is disclosed comprising inserting a needle from a patient's exterior surface of a suprapubic skin through the patient's abdominal region and into the patient's urinary bladder to create a tract. Threading a guide wire through the needle so the guide wire travels from the suprapubic skin into the urinary bladder and removing needle while leaving the guide wire in the tract. Dilating the tract to a desired width and measuring a distance between the patient's suprapubic skin and the patient's urinary bladder via the tract. And inserting a medical device suitable for use based on the previously measure distance.

In another embodiment a method for replacing a medical device comprises placing a guide wire from a patient's suprapubic skin through the patient's abdominal region and into the patient's urinary bladder, the guide wire traveling from the suprapubic skin into the urinary bladder within a previously placed medical device. And removing the previously placed medical device by sliding the device along the guide wire and away from the patient; filling the bladder of the patient and measuring a distance between the patient's suprapubic skin and the patient's urinary bladder; selecting a second medical device suitable for use based on the previously measured distance and inserting the selected medical device; and draining the urinary bladder of the patient.

It should be noted that the suprapubic location of the medical device decreases infection rates in comparison to intraurethral catheterization. In addition, the low profile design of the medical device has less material for contact and infection. In addition, an antimicrobial may be applied to the entire device or the tube to reduce the possibility of infection and increase the length of use over traditional suprapubic tubes.

Figure 17:
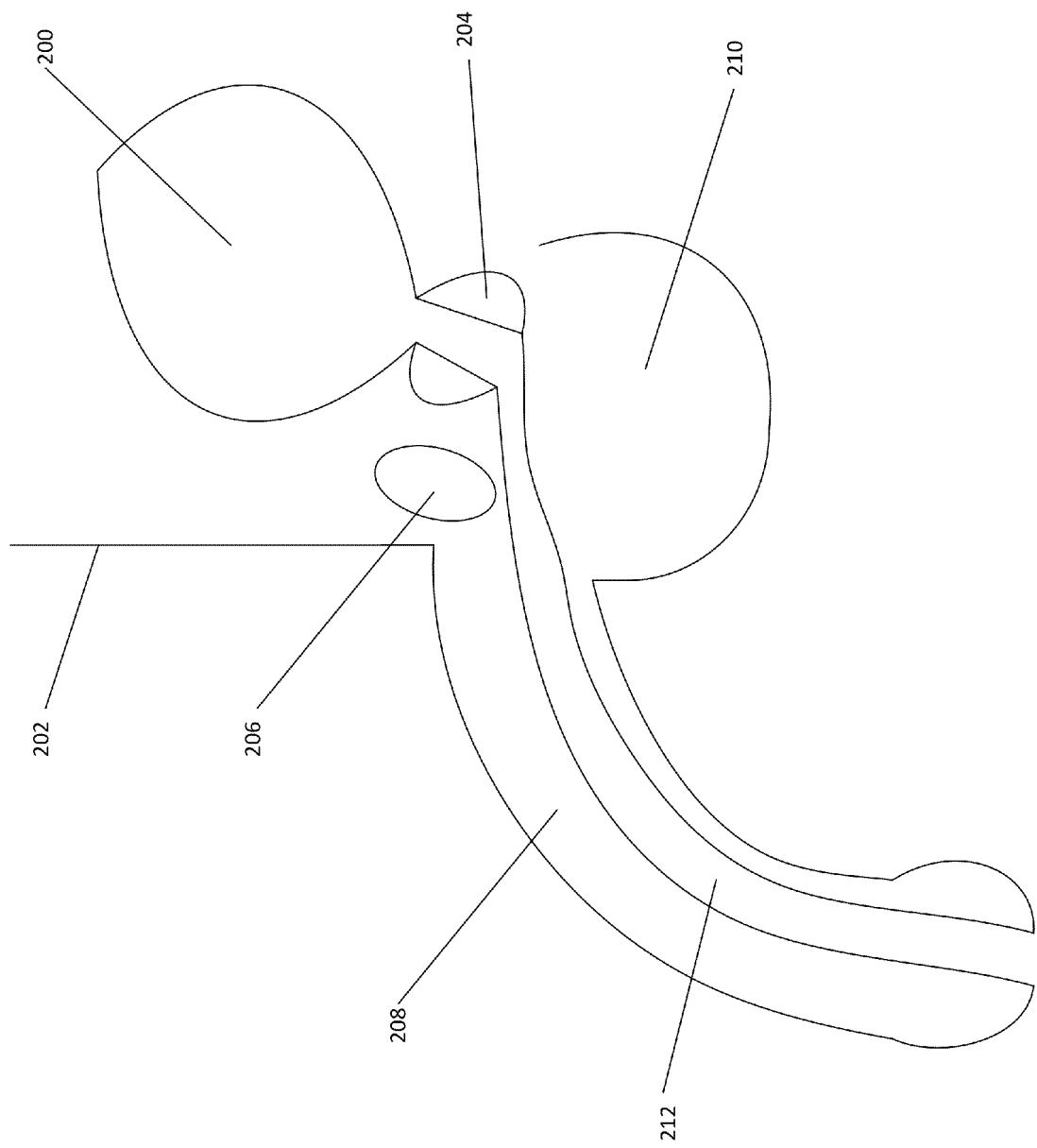
FIG. 17 illustrates the general anatomy of a male penis and bladder.

Referring now to FIG. 17 which generally shows a side view of the male penis and surrounding anatomy. The surface of the patient's pelvic skin 202 overlays the male pubic bone 206 and connects to the penis 208. The male urethra 212 extends from the tip of the penis 208 into the male body, past the prostate gland 204 and into the male bladder 200.

Figure 18:
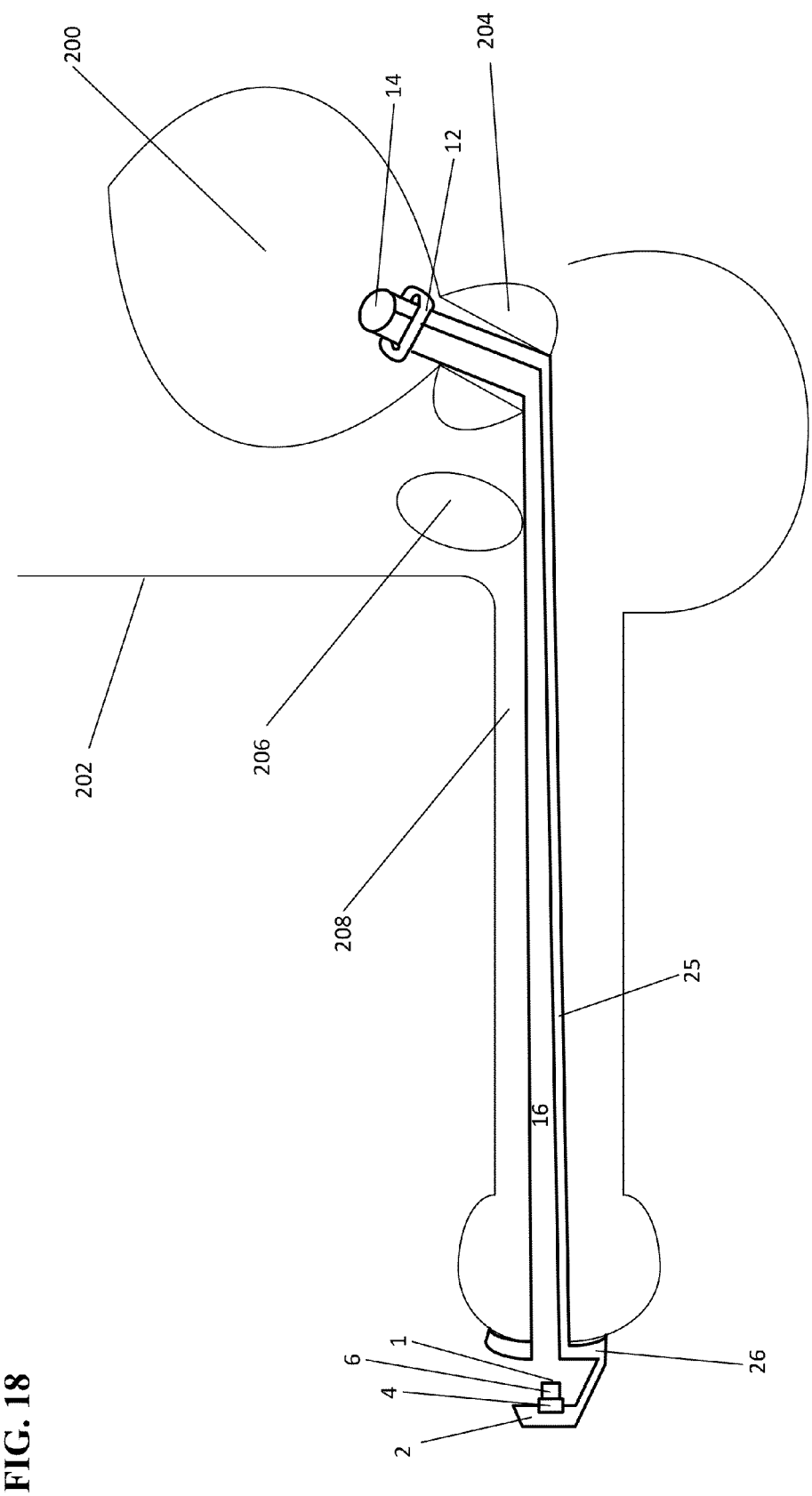
FIG. 18 illustrates the general anatomy of a male penis and bladder (side view) with a medical device inserted up the urethra of the male penis and terminating in the bladder. The first cap is unsecured to the hollow tube and the balloon is deflated.

Referring to FIG. 18, in an embodiment of the present disclosure, a medical device is designed for insertion into the urethra 212 of the male penis 208 and terminates in the bladder 200 of the patient. An embodiment of a medical device for insertion into the male urethra is like the previously discussed embodiments for insertion between an exterior surface of a patient's suprapubic region 8 and the patient's urinary bladder 10.

In an embodiment designed for insertion into a male's urethra, a continuous hollow tube 16, spanning the distance between an exterior surface of a patient's penis 208 and the patient's urinary bladder 200 may have a diameter between 1 french and 70 french and a length between 0.5 cm and 50 cm. Embodiments contemplated by this disclosure are not limited to the disclosed diameters and lengths. The appropriate diameter and length will be dependent on the application and patient's anatomy and/or physique. The diameter of the hollow tube 16 and the length of the hollow tube 16 will vary depending on the patient's anatomy and physical condition. For example, a physician may determine the appropriate length of the hollow tube 16, and therefore the corresponding size of the medical device, by measuring the distance from the tip of the male patient's penis to the bladder using a depth gauge or graduated measuring device (e.g., FIG. 28).

In an embodiment, a medical device of the present disclosure designed for insertion into a male's urethra will not have a one way valve 24 (not pictured) while in other embodiments it may. Still referring to FIG. 18, following insertion of the medical device into the male patient's urethra, the first cap 2 is not secured to the proximal end 3 of the tube 16. The distal end 14 terminates within the male patient's urethra so that the inflated balloon-like component 12 is within the patient's urethra (deflated in FIG. 18.)

Figure 19:
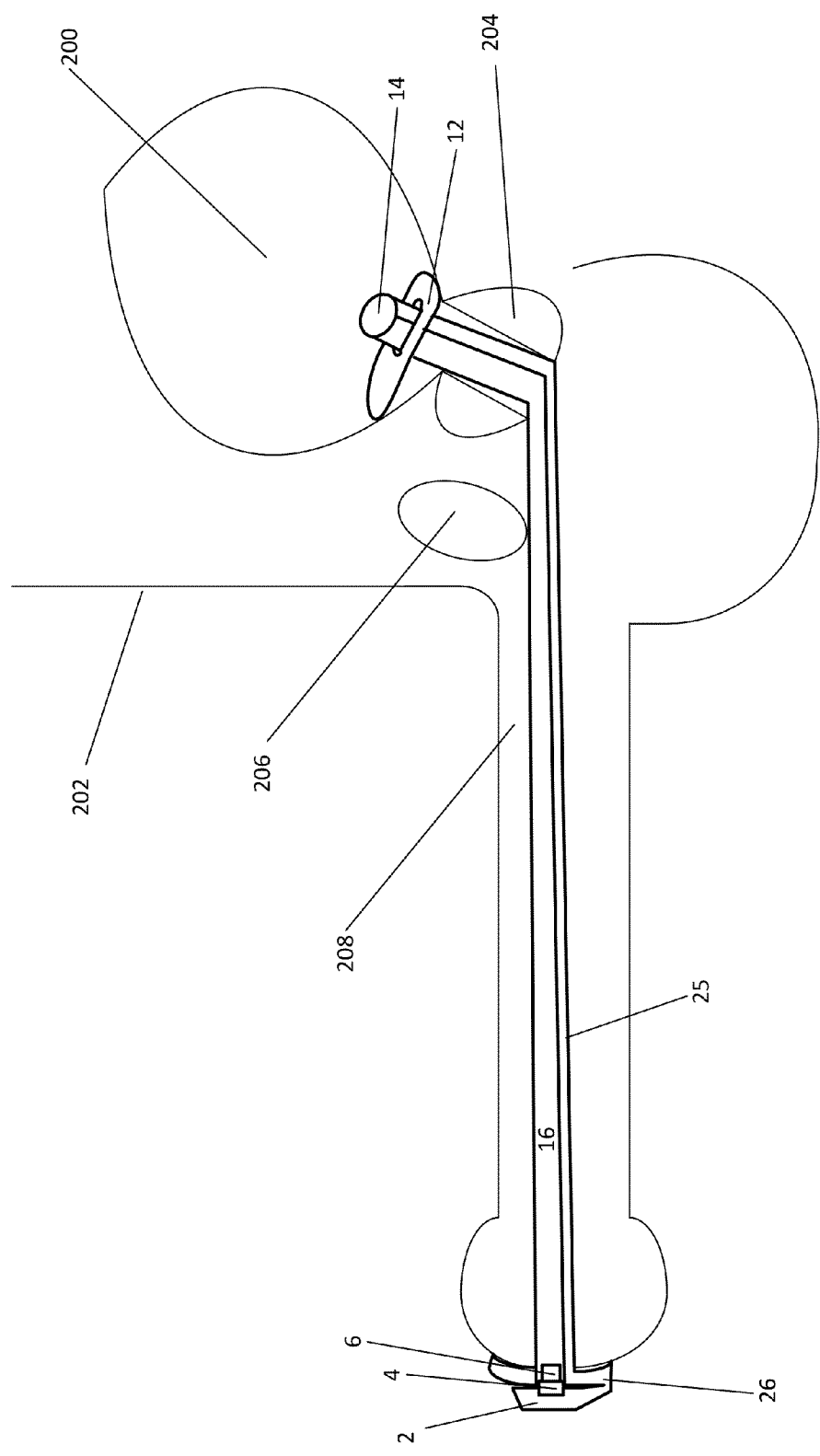
FIG. 19 illustrates the general anatomy of a male penis and bladder (side view) with a medical device up the urethra of the male penis and terminating in the bladder. The first cap is secured to the hollow tube and the balloon is inflated.

Referring now to FIG. 19, following insertion of the medical device, the balloon-like component 12 is inflated via the inflation port 6 so that the balloon-like component 12 keeps the medical device in place and prevents accidental removal. In a preferred embodiment, the medical device is sized to the patient's anatomy so that following inflation of the balloon-like component the proximal end 3 of the medical device (including the first cap 2, the inflation port valve 4, the inflation port 6) fit snugly against the tip of the male patient's penis 208. A snug fit is preferred so that the medical device is low-profile and does not unnecessarily snag on clothing or external objects. In some embodiments, retention wings 34 (not shown) help keep the medical device snugly placed.

Referring now to FIG. 20, in an embodiment the proximal end of the hollow tube 16 will have a locking mechanism (e.g., FIG. 6 and FIG. 7) which in some embodiments is recessed slots 41. As previously described the locking mechanism allows external devices, e.g., drainage tubing, to operatively attach to the medical device.

Referring now to FIG. 21, one aspect of the present disclosure is a universal connector 210. While the universal connector shown in FIG. 21 has a conical shape, it may have a variety of different shapes. The universal connector 210 has a proximal end 216 and a distal end 218. Adjacent to the distal end 218 the universal connector has an engagement apparatus 212 that includes protrusions 214 designed to operatively interact with the recessed slots 41 in the medical device. Upon insertion the distal end 218 of the universal connector 210 a medical device of the present disclosure, the engagement apparatus 212 and its protrusions 214 will securely affix the universal connector to the medical device so that fluid may flow from a patient's body, through the medical device and out of the proximal end 216 of the universal connector 210. The embodiment of the engagement apparatus 212 and locking mechanism (recessed slots 41) shown in FIG. 21 is merely representative of the type of engagement male/female engagement contemplated by this disclosure. The important aspect of this disclosure is that the engagement apparatus of the universal connector 210 is capable of operatively interacting with the locking mechanism of the medical device. For example, the locking mechanism may be similar to recessed slots 41 or similar to the twist locking mechanism 38 (e.g., FIG. 6) or push-button locking mechanism (e.g., FIG. 7). The engagement apparatus 212 will vary depending on the locking mechanism used by the medical device.

In some instances, the universal connector 210 is made of a resilient and pliable material, like silicone or rubber, that allows a user to pinch the sides of the distal end of the universal connector together to facilitate insertion of the distal end 218 of the universal connector 210 into the proximal end 3 of the medical device, thereby allowing the engagement apparatus 212 to operatively interact with the locking mechanism.

Referring now to FIG. 22, in some embodiments the engagement apparatus 212 will be capable of moving (e.g., because the engagement apparatus has elastic properties like a rubber band) along a distance D1 from the distal end 218 of the universal connector 210. In some embodiments, this will allow a user to push the distal end 218 of the universal connector 210 farther into the proximal end 3 of the medical device before the engagement apparatus 212 engages the locking mechanism (e.g., 41.)

Referring now to FIG. 23, the proximal end 216 of the universal connector 210 is designed to accept a variety of different size and shaped medical tubing 220 so that a universal connector 210 may be used to operatively and/or fluidly connect a variety of medical tubing to a medical device of the present disclosure. For example, a user may unsecure the first cap 2 of a medical device placed in the urethra (or other place as descried in this disclosure) of a patient. The user may then operatively affix a universal connector 210 to the proximal end of the medical device using an engagement apparatus 212 compatible with the locking mechanism of the medical device within the patient (e.g., FIG. 6, FIG. 7 and FIG. 20). Once the universal connector is affixed to the medical device, a user may then place the distal end 222 of any variety of different diameter medical tubing 220 into the proximal end 216 of the universal connector 210. The user may then drain fluid from a patient's body whereby the fluid leaves the bladder 200 of the patient, traveling from the distal end 14 to the proximal end 3 of the medical device, through the universal connector 210 and into the medical tubing 220.

Figure 24:
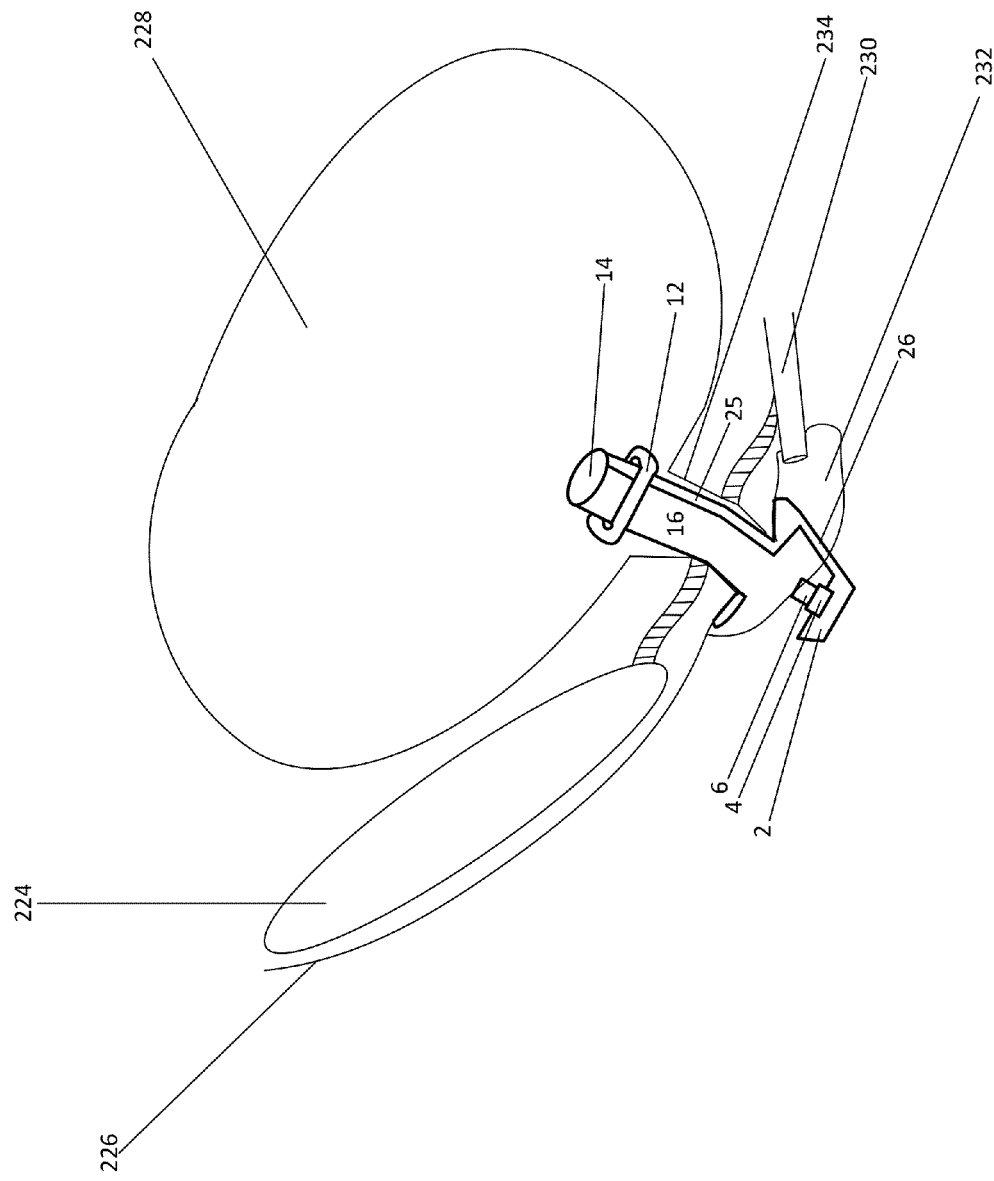
FIG. 24 illustrates the general anatomy of the female genitalia (side view) and bladder with a medical device inserted up the urethra and terminating in the bladder. The first cap is unsecured to the hollow tube and the balloon is deflated.

Referring now to FIG. 24, in an embodiment of the present disclosure, a medical device is designed for insertion into the urethra 234 of a female and terminates in the bladder of the patient 228. An embodiment of a medical device for insertion into the female urethra is like the previously discussed embodiments for insertion between an exterior surface of a patient's suprapubic region 8 and the patient's urinary bladder 10.

In an embodiment designed for insertion into a female's urethra, a continuous hollow tube 16, spanning the distance between an exterior surface of a patient's labia 232, just above the patient's vagina 230 to the patient's urinary bladder 228 may have a diameter between 1 french and 70 french and a length between 0.5 cm and 50 cm. Embodiments contemplated by this disclosure are not limited to the disclosed diameters and lengths. The appropriate diameter and length will be dependent on the application and patient's anatomy and/or physique. The diameter of the hollow tube 16 and the length of the hollow tube 16 will vary depending on the patient's anatomy and physical condition. For example, a physician may determine the appropriate length of the hollow tube 16, and therefore the corresponding size of the medical device, by measuring the distance from the surface of the female patient's labia 232 to the bladder 228 using a depth gauge or graduated measuring device (e.g., FIG. 28). FIG. 24 generally discloses a female patient's anatomy (pubic bone 224, skin 226, vagina 230 and labia 232) following insertion of a medical device of the present disclosure up the urethra of the patient and terminating in the patient's bladder. This embodiment medical device may have the same attributes and features as described previously for different embodiments of the medical device.

Figure 25:
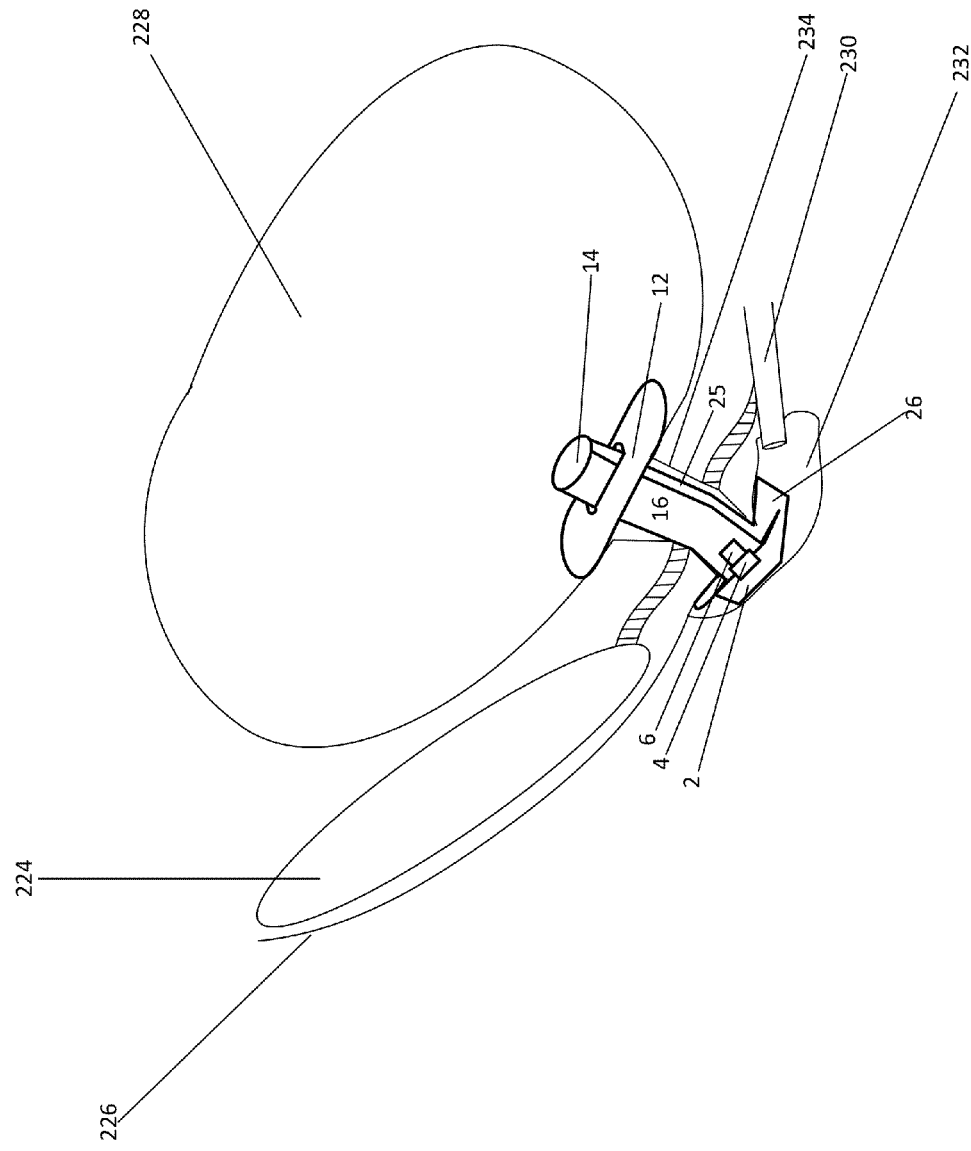
FIG. 25 illustrates the general anatomy of the female genitalia (side view) and bladder with a medical device inserted up the urethra and terminating in the bladder. The first cap is secured to the hollow tube and the balloon is inflated.

Referring now to FIG. 25, following insertion of the medical device, the balloon-like component 12 is inflated via the inflation port 6 so that the balloon-like component 12 keeps the medical device in place and prevents accidental removal. In a preferred embodiment, the medical device is sized to the patient's anatomy so that following inflation of the balloon-like component the proximal end 3 of the medical device (including the first cap 2, the inflation port valve 4, the inflation port 6) fit snugly against the skin of the female patient's anatomy 232. A snug fit is preferred so that the medical device is low-profile and does not unnecessarily snag on clothing or external objects. In some embodiments, retention wings 34 (not shown) help keep the medical device snugly placed.

Figure 26:
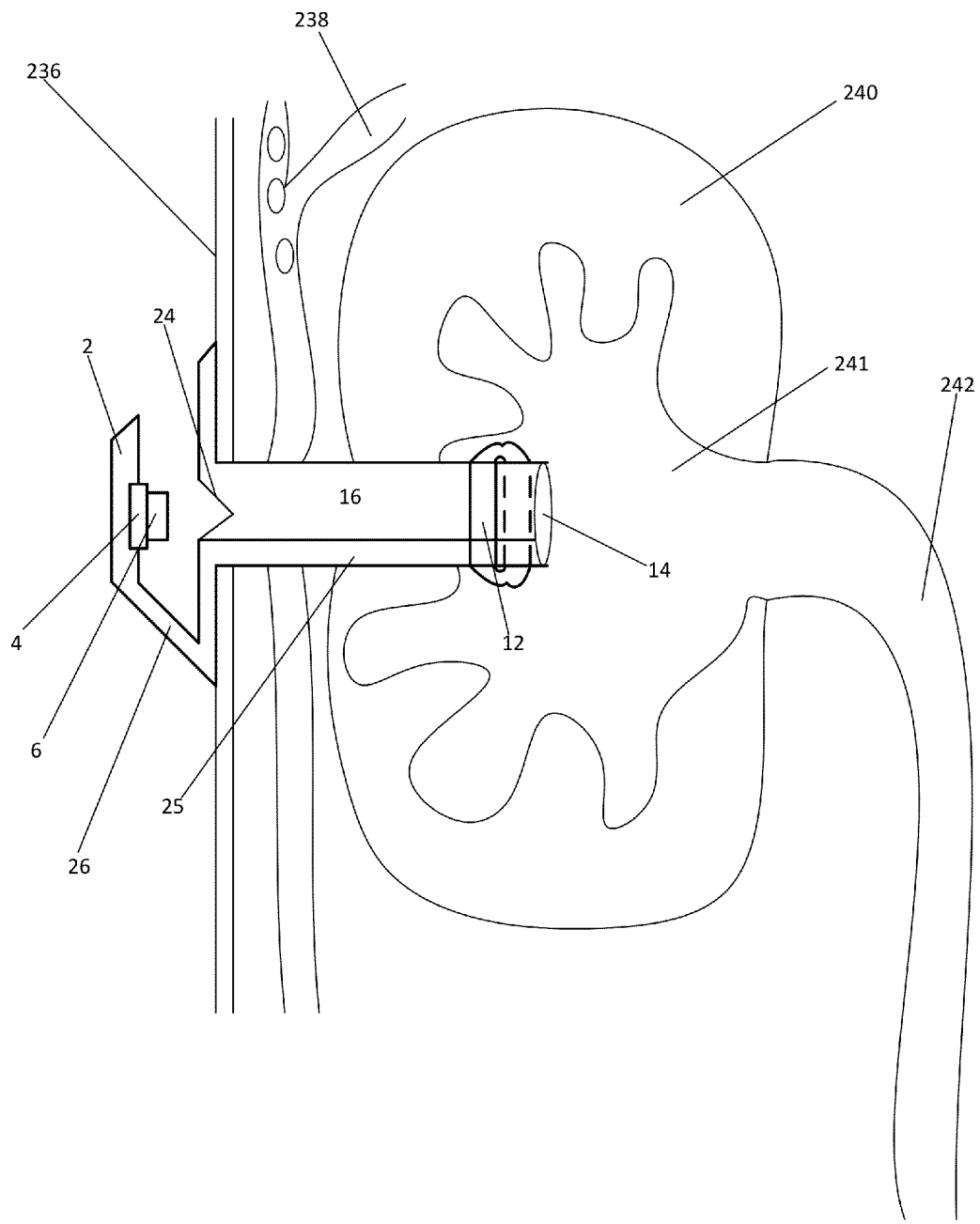
FIG. 26 illustrates the general anatomy of a patient's kidney and back (side view) with a medical device inserted through the back of the patient and terminating in the kidney. The first cap is unsecured to the hollow tube and the balloon is deflated.

Referring now to FIG. 26, in an embodiment of the present disclosure, a medical device is designed for percutaneous insertion into a patient's kidney 240 and terminates in the pelvis of the kidney 240. In this embodiment, a medical device of the present disclosure may replace the use of nephrostomy tubes. Generally, medical personal may use a medical device of the present disclosure for percutaneous insertion into the pelvis of a patient's kidney to achieve direct access to apart of the upper urinary tract for various procedures. In addition, kidney stones or other blockages can stop the flow of urine from the kidneys through ureters and into the bladder. This can cause pain and a condition known as hydronephritis. By using a medical device of the present disclosure to establish fluid connection to the pelvis of the Kidney, medical personal may bypass a blocked area and allow urine to leave the body through the medical device. An embodiment of a medical device for percutaneous insertion into the pelvis of a patient's kidney is like the previously discussed embodiments for insertion between an exterior surface of a patient's suprapubic region 8 and the patient's urinary bladder 10.

In an embodiment designed for percutaneous insertion into the pelvis 241 of a patient's kidney 240, a continuous hollow tube 16, spanning the distance between an exterior surface of a patient's skin 236 (patient's back) and the pelvis 241 of the kidney 240 may have a diameter between 1 french and 70 french and a length between 0.5 cm and 50 cm. Embodiments contemplated by this disclosure are not limited to the disclosed diameters and lengths. The appropriate diameter and length will be dependent on the application and patient's anatomy and/or physique. The diameter of the hollow tube 16 and the length of the hollow tube 16 will vary depending on the patient's anatomy and physical condition.

FIG. 26 generally discloses a side view of a patient's kidney and the surrounding anatomy (skin of a patient's back 236, kidney 240, pelvis 241 of kidney 240) following the percutaneous insertion of a medical device of the present disclosure through a patient's back 236 and terminating in the pelvis 241 of a patient's kidney 240. This embodiment of the medical device may have the same attributes and features as described previously for different embodiments of the medical device.

In an embodiment, a medical device of the present disclosure designed for percutaneous insertion into the pelvis of a patient's kidney will have a valve 24. Still referring to FIG. 26, following the percutaneous insertion of the medical device into the pelvis 241 of the kidney 240, the first cap 2 is not secured to the proximal end 3 of the tube 16. The distal end 14 terminates within the pelvis of the kidney so that the inflated balloon-like component 12 is within the pelvis 241 (deflated in FIG. 26).

Figure 27:
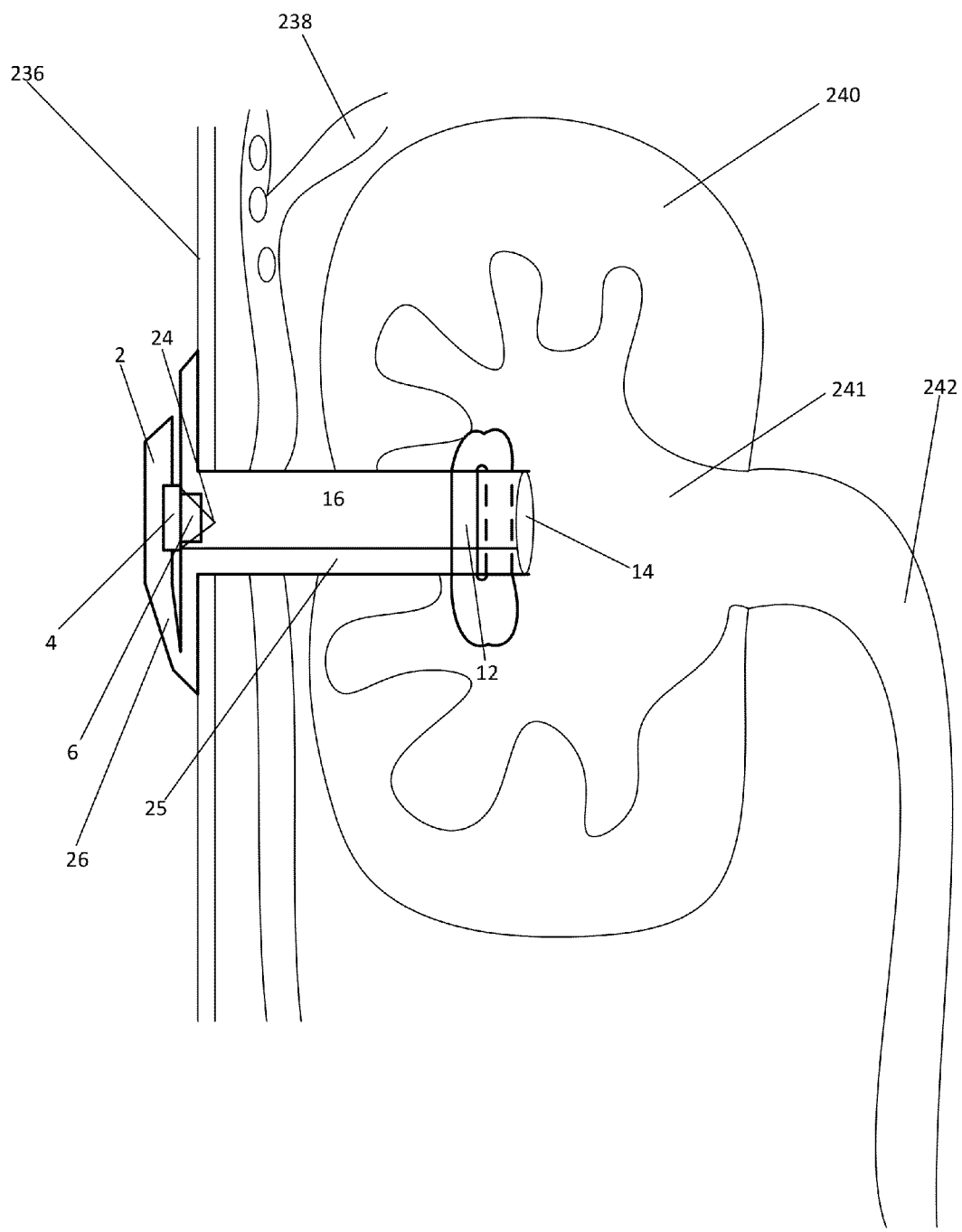
FIG. 27 illustrates the general anatomy of a patient's kidney and back (side view) with a medical device inserted through the back of the patient and terminating in the kidney. The first cap is secured to the hollow tube and the balloon is inflated.

Referring now to FIG. 27, following insertion of the medical device, the balloon-like component 12 is inflated via the inflation port 6 so that the balloon-like component 12 keeps the medical device in place and prevents accidental removal. In an embodiment, the medical device is sized to the patient's anatomy so that following inflation of the balloon-like component the proximal end 3 of the medical device (including the first cap 2, the inflation port valve 4, the inflation port 6) fit snugly against the patient's skin 236. A snug fit is preferred so that the medical device is low-profile and does not unnecessarily snag on clothing or external objects. In some embodiments, retention wings 34 (not shown) help keep the medical device snugly placed.

In one embodiment, the medical device for percutaneous insertion into the pelvis of a patient's kidney does not comprise a inflatable balloon-like component. In this embodiment, the device is held snugly in place using sutures to suture the device to the patient's skin.

Figure 28:
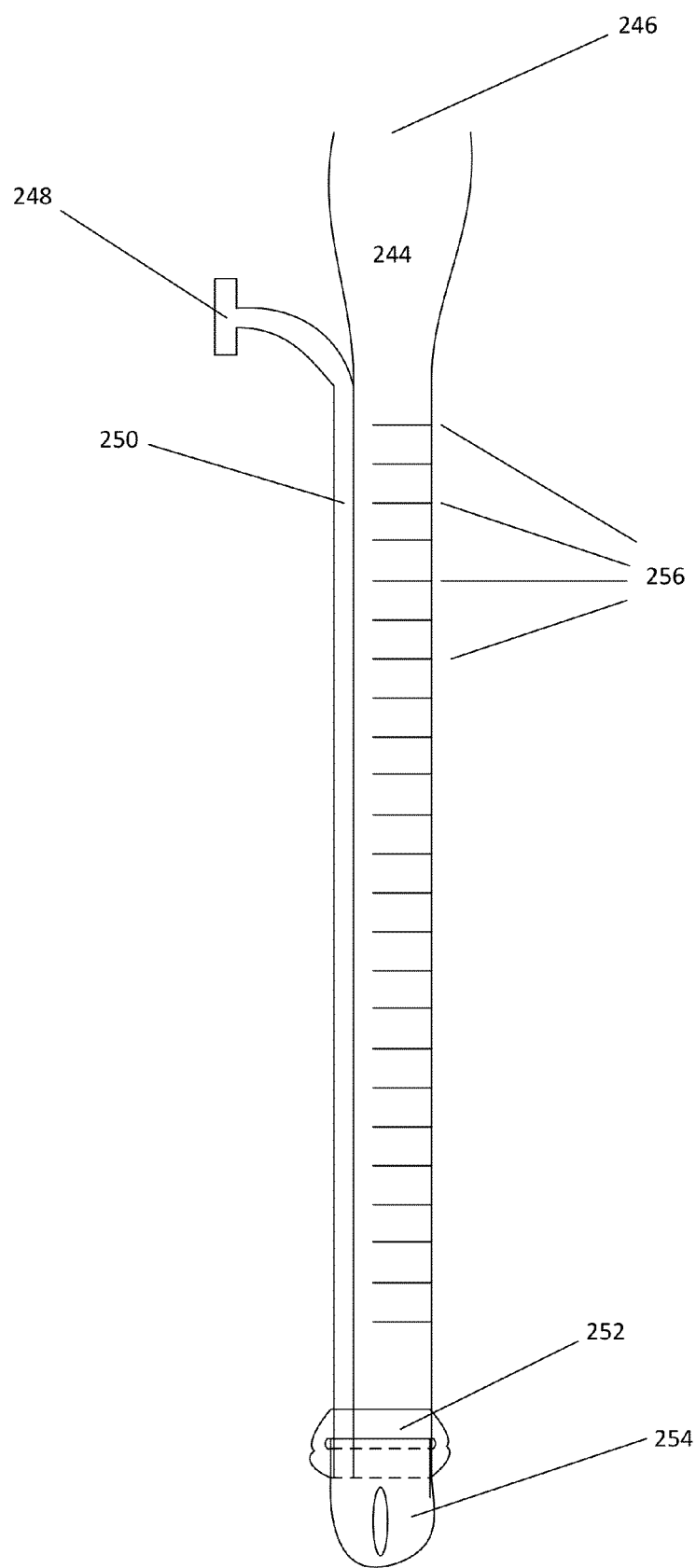
FIG. 28 illustrates a graduated measuring device of the present disclosure with graduated markings for accurately determining the distance between the patients skin and the termination point for a medical device.

Referring now to FIG. 28, another component of the present disclosure is a graduated measuring device 244 or a depth gauge for determining the distance between points in a patient's anatomy and ultimately determining what size medical device will provide the best fit for the patient, e.g., ensuring a snug fit. The measuring device of the present disclosure has a proximal end 246 and a distal end 254 with a first channel running between the proximal 246 and distal ends 254. The measuring device further comprises a second channel 250 that runs between a port 248 and a balloon-like inflatable component 252. The measuring device further comprises graduated marks 256 for measurement. The diameter of the measuring device may be between 1 french and 70 french and a length between 0.5 cm and 50 cm. Embodiments contemplated by this disclosure are not limited to the disclosed diameters and lengths. The appropriate diameter and length will be dependent on the application and patient's anatomy and/or physique.

In an embodiment, the user will place the device into a patient's urethra until the distal end 254 of the measuring device 244, including the balloon-like inflatable component 252 is within the patient's bladder. The user will then inflate the balloon-like inflatable component by injecting liquid or air through the port 248, down the second channel 250 and into the balloon-like inflatable component 252. Once the balloon-like component 252 is inflated the user can pull on the device 244 to snug the inflated balloon-like component (e.g., a balloon) against the inner wall of the patient's bladder. Using the graduate marks the user may then determine the distance between the patient's skin, e.g., tip of a patient's penis, and the patient's bladder. This distance may be used to determine the appropriate sized medical device to insert into the patient for longer term use. In an embodiment, the patient may leave the graduated measuring device in place while waiting for the appropriate size medical device to arrive.

Figure 29:
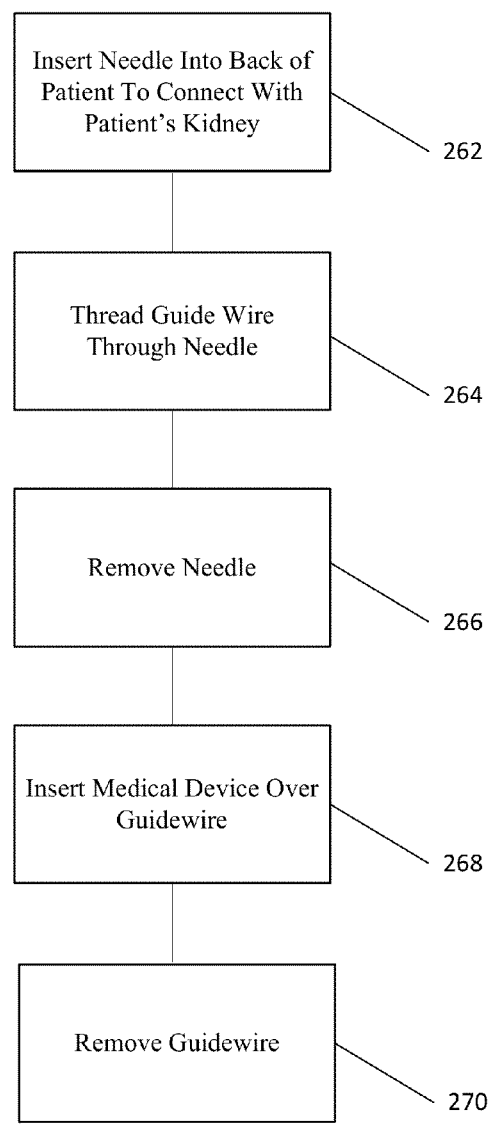
FIG. 29 illustrates steps medical personnel may take for inserting a medical device of the present disclosure through the back and into the kidney of a patient.

Referring now to FIG. 29, which discloses a method 260 of the present disclosure. In method 260 a patient inserts a needle 262, e.g., large bore needle, into the back of a patient, piercing the patient's skin and creating a passageway from the patient's skin to the pelvis of the patient's kidney. The user will then thread a guide wire through the needle 264 followed by removing the needle while leaving the guide wire in place 266. The user may then insert a medical device of the present disclosure (e.g., FIG. 26) over the guide wire 268 and then remove the guide wire 270. In some embodiments, a user may determine the distance between the patient's skin and the pelvis of the kidney using a graduate measuring device prior to inserting the guide wire 268.

Figure 30:
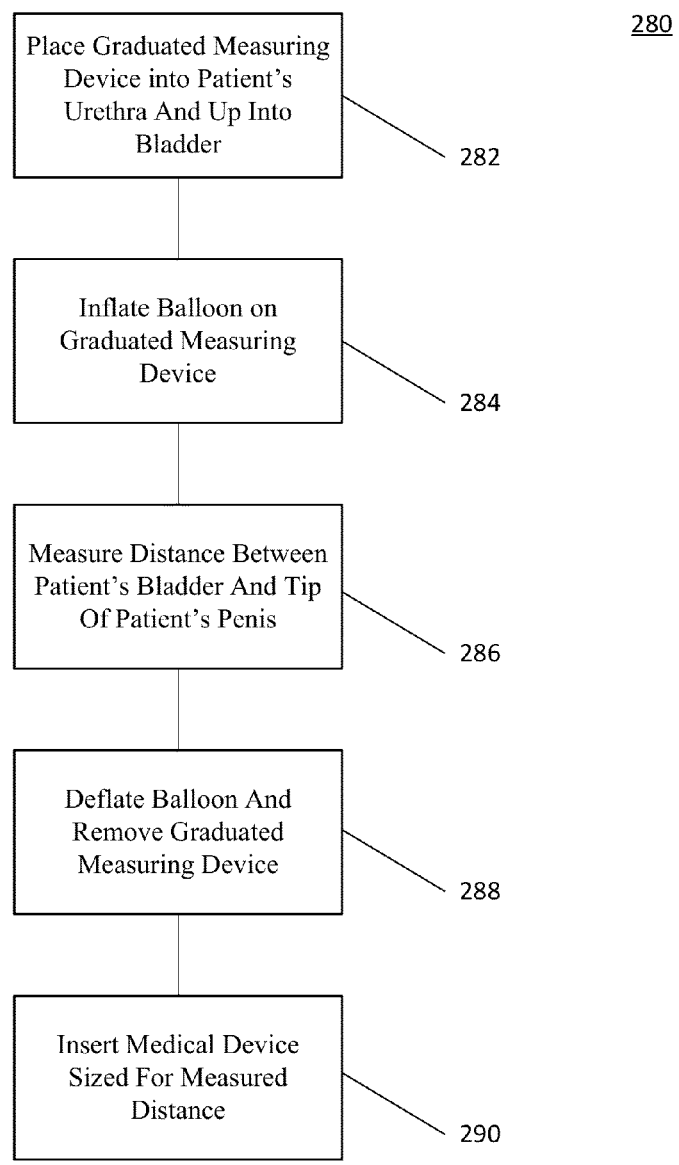
FIG. 30 illustrates steps medical personnel may take for inserting a medical device of the present disclosure up the urethra and into the bladder of a patient.

Referring now to FIG. 30, which discloses a method 280 of the present disclosure. In method 280, a user insert's a graduate measuring device into a patient urethra, extending into a patient's bladder 282. The user then inflates the balloon-like component of the graduated measuring device 284 and measures the distance between the patient's bladder and tip of the patient's penis 286. The user then deflates the balloon-like component and removes the graduate measuring device 288. The user then insert's a medical device of the present disclosure sized according to the distance measured using the graduated measuring device 290.

Figure 31:
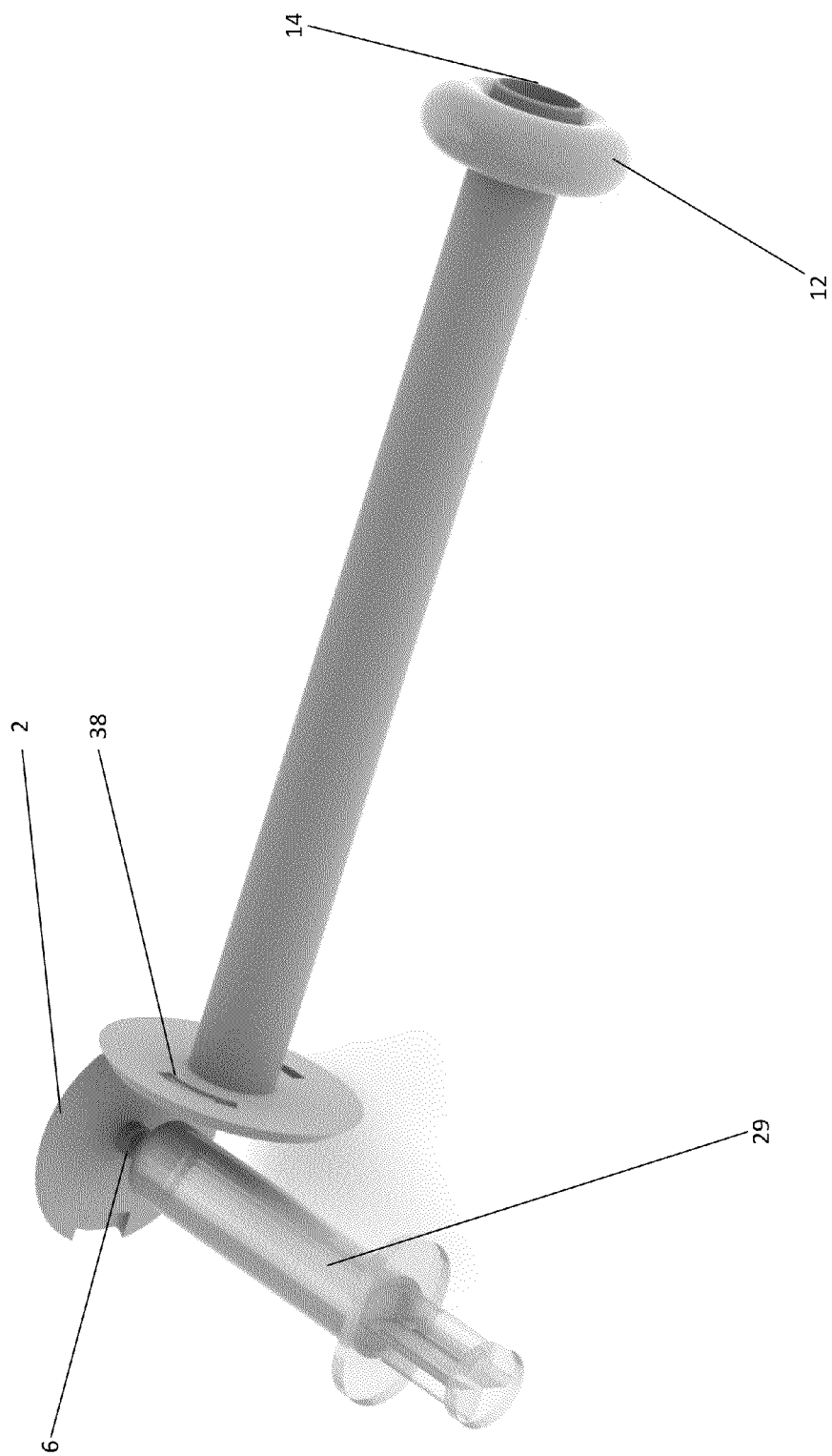
FIG. 31 illustrates a side profile of an embodiment of the medical device like FIG. 3 with the first cap unsecured to the hollow tube and a syringe operatively connected to the first cap. The balloon-like component is inflated.
Figure 32:
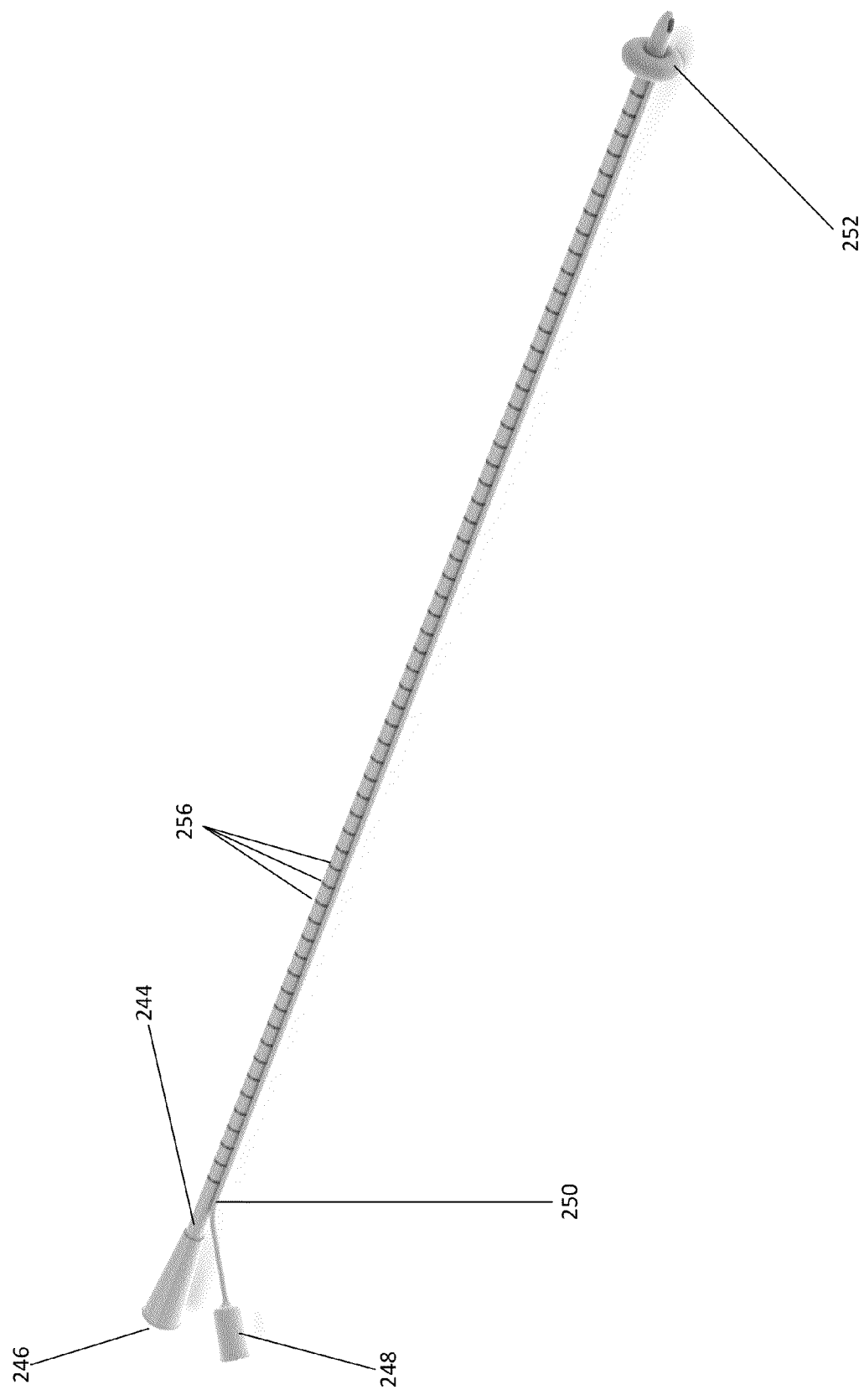
FIG. 32 illustrates a view of a graduated measuring device of the present disclosure like FIG. 28 with graduated markings for accurately determining the distance between the patients skin and the termination point for a medical device. The balloon-like component is inflated.

Referring now to FIG. 31, which discloses an embodiment as previously discussed using like numbers and that is particularly suitable for insertion into a patient's suprapubic region to reach the patient's bladder. The balloon-like component 12 is shown inflated as it would be after insertion into a patient. The second (separate) channel 25 that runs along the length of the device to fluidly connect the balloon-like component 12 and the liquid injected using a syringe 29 is not visible but is present. Referring now to FIG. 32, which discloses an embodiment of a graduated measuring device 244 as previously discussed in FIG. 28.

Figure 33:
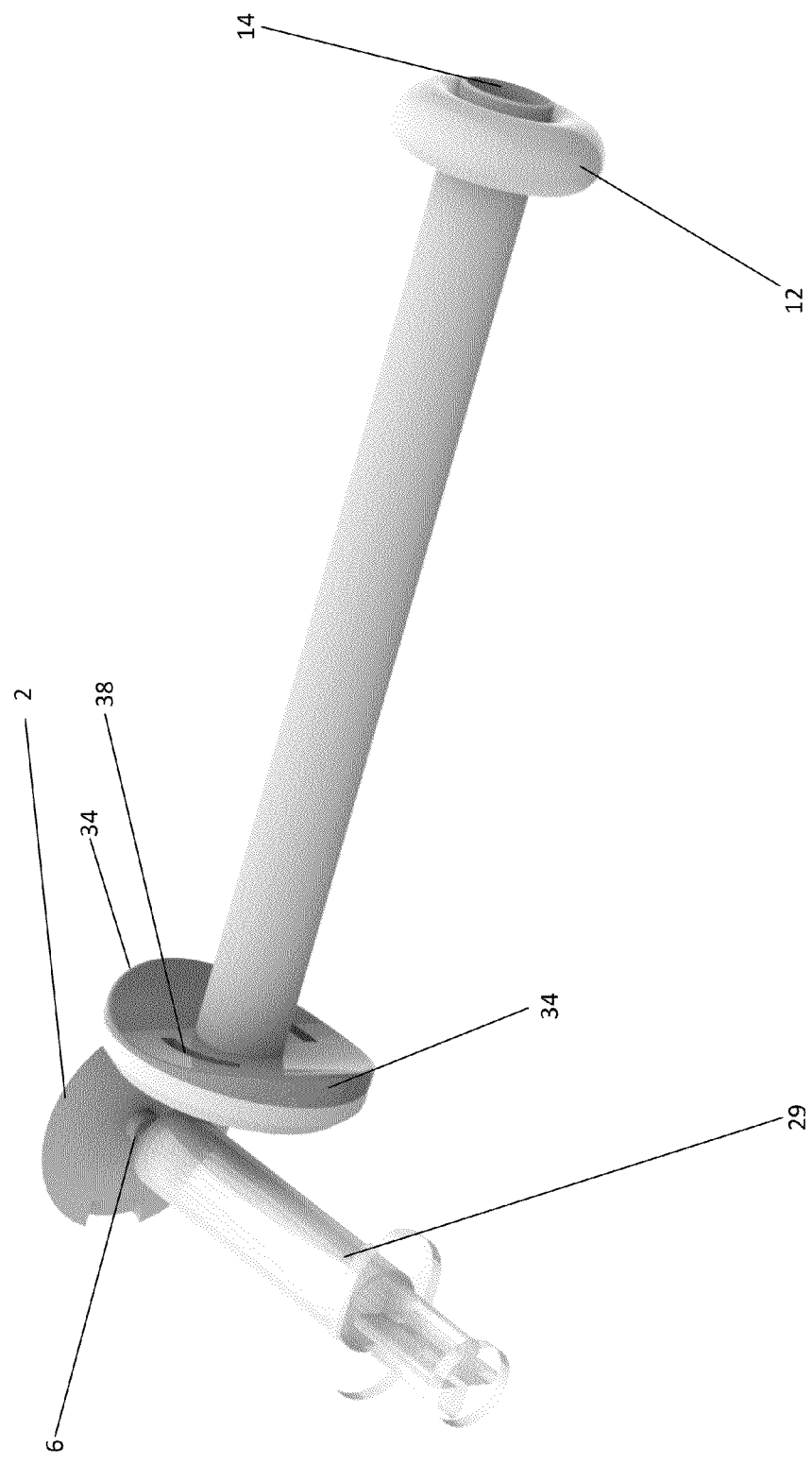
FIG. 33 illustrates a side profile of an embodiment of the medical device like FIG. 3 with the first cap unsecured to the hollow tube and a syringe operatively connected to the first cap. The balloon-like component is inflated.

Referring now to FIG. 33 which discloses an embodiment as previously discussed using like numbers and that is particularly suitable for insertion into a patient's urethra. Notably, a twist locking mechanism 38 is shown that allows the connection of external devices via the twist lock 38. This locking mechanism, usually made of plastic but can also be made of a variety of materials, e.g., latex, rubber, silicone or the like, has key holes that match the external drainage tubing teeth or protrusions 214 from the engagement apparatus 212 on a universal connector 210. Still referring to FIG. 32, the retention wings 34 that span out from the proximal end 3 of the tube 16 may have a concave under surface (surface that contacts skin) to better fit a patient's skin texture and curvature. This embodiment would be particular helpful when the medical device is used for insertion into a male urethra.

Figure 34:
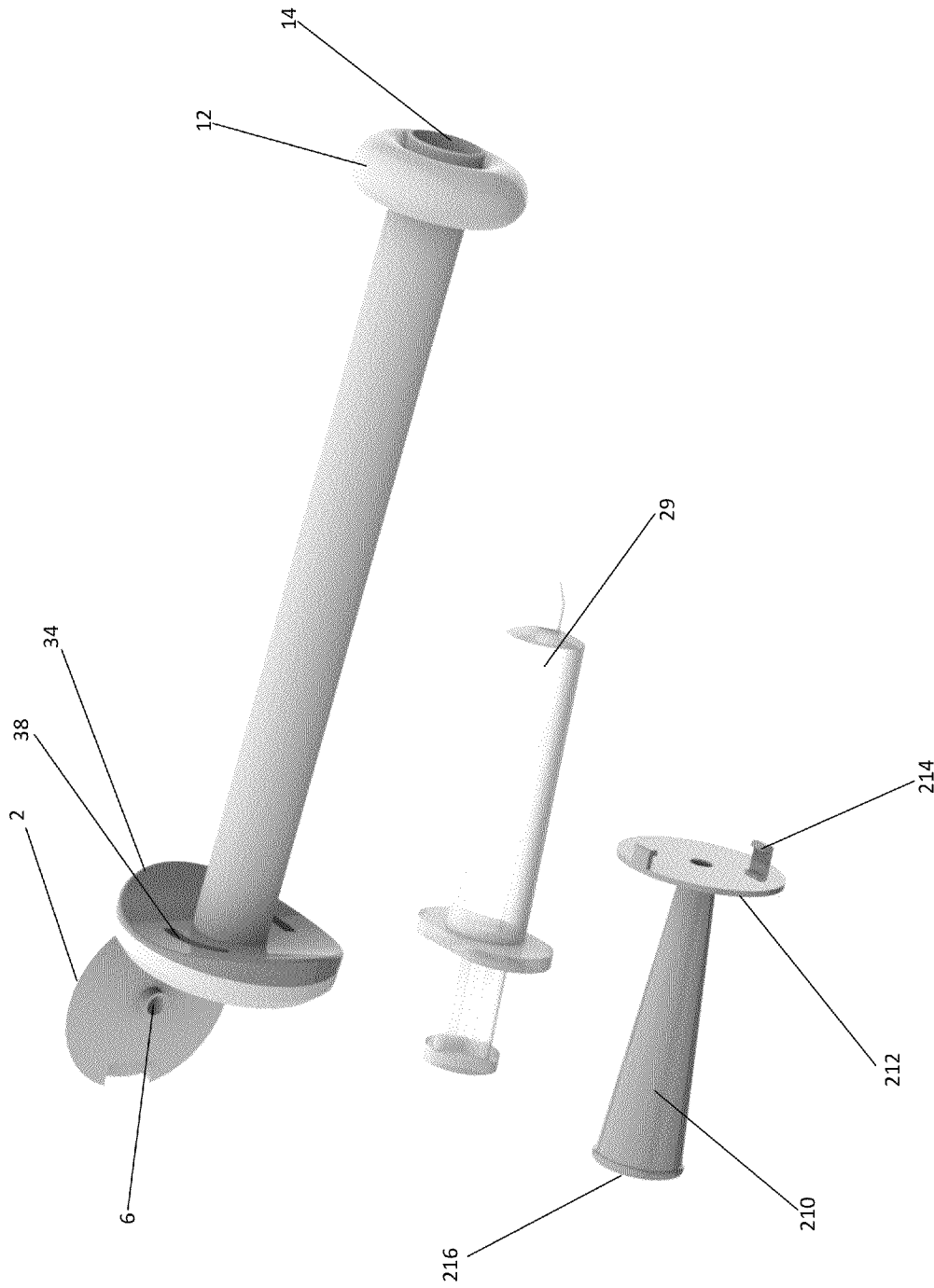
FIG. 34 illustrates an embodiment of the medical device with the first cap unsecured to the hollow tube, a syringe, and a universal connector.
Figure 35:
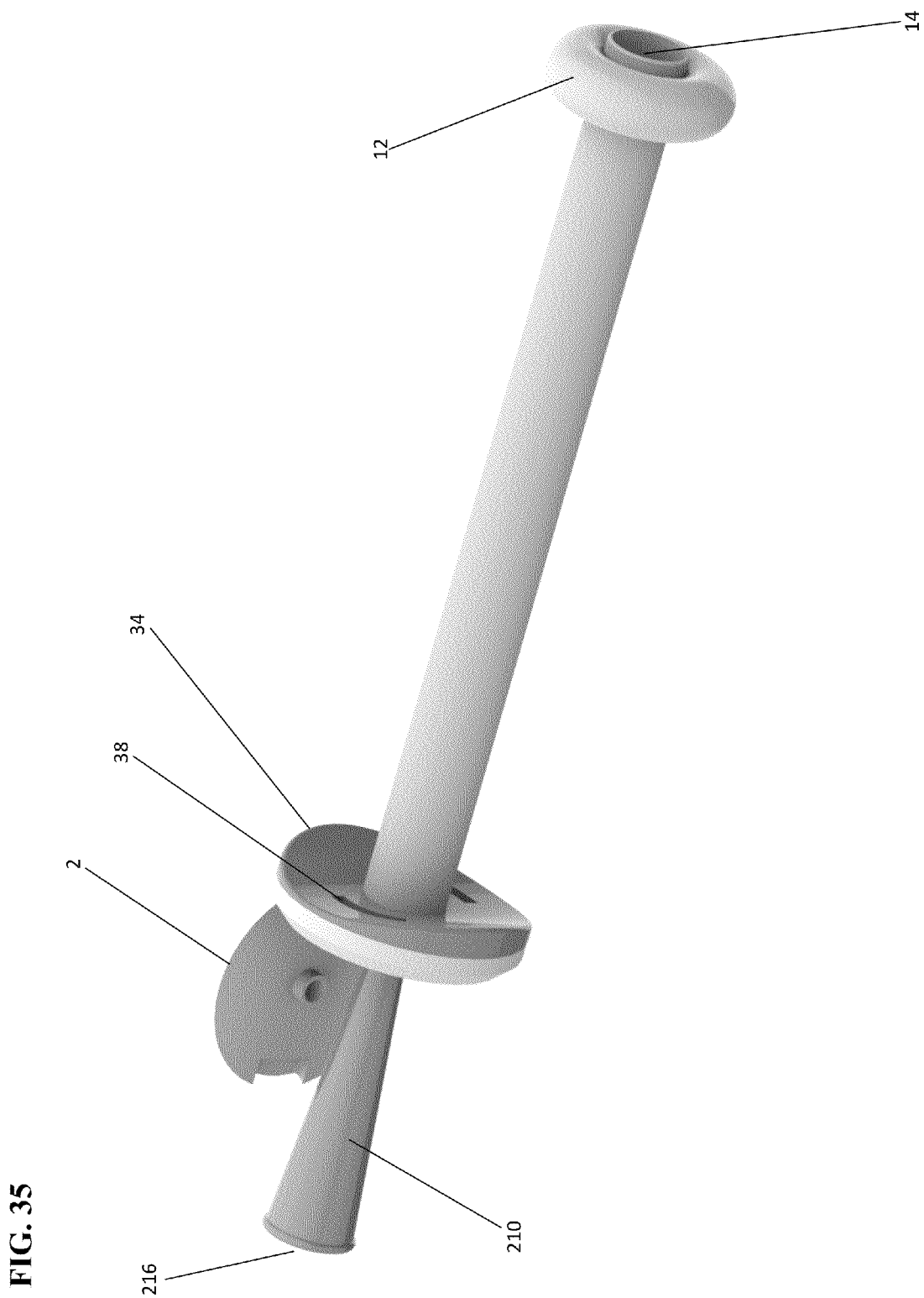
FIG. 35 illustrates an embodiment of the medical device with the first cap unsecured to the hollow tube and a universal connector operatively connected to the medical device through an embodiment of the locking mechanism.

Referring now to FIG. 34 and FIG. 35 which disclose embodiments as previously discussed using like numbers and that are particularly suitable for insertion into a patient's urethra. A particular embodiment of the universal connector 210 is shown both prior to and after it has been operatively attached to an embodiment of the medical device.

Figure 36:
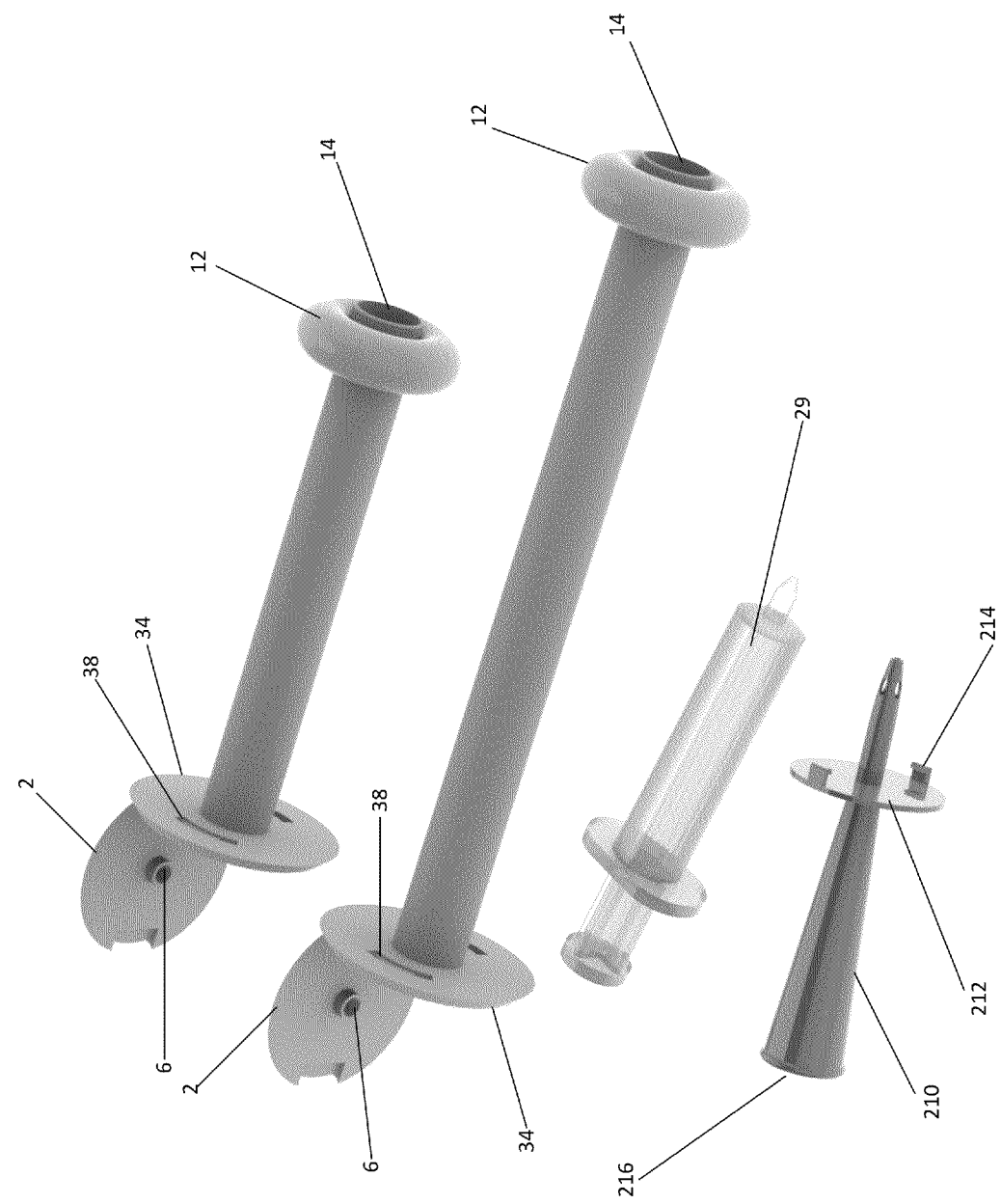
FIG. 36 illustrates an embodiment of the medical device in two different sizes with the first caps unsecured to the hollow tubes, a syringe, and a universal connector.
Figure 37:
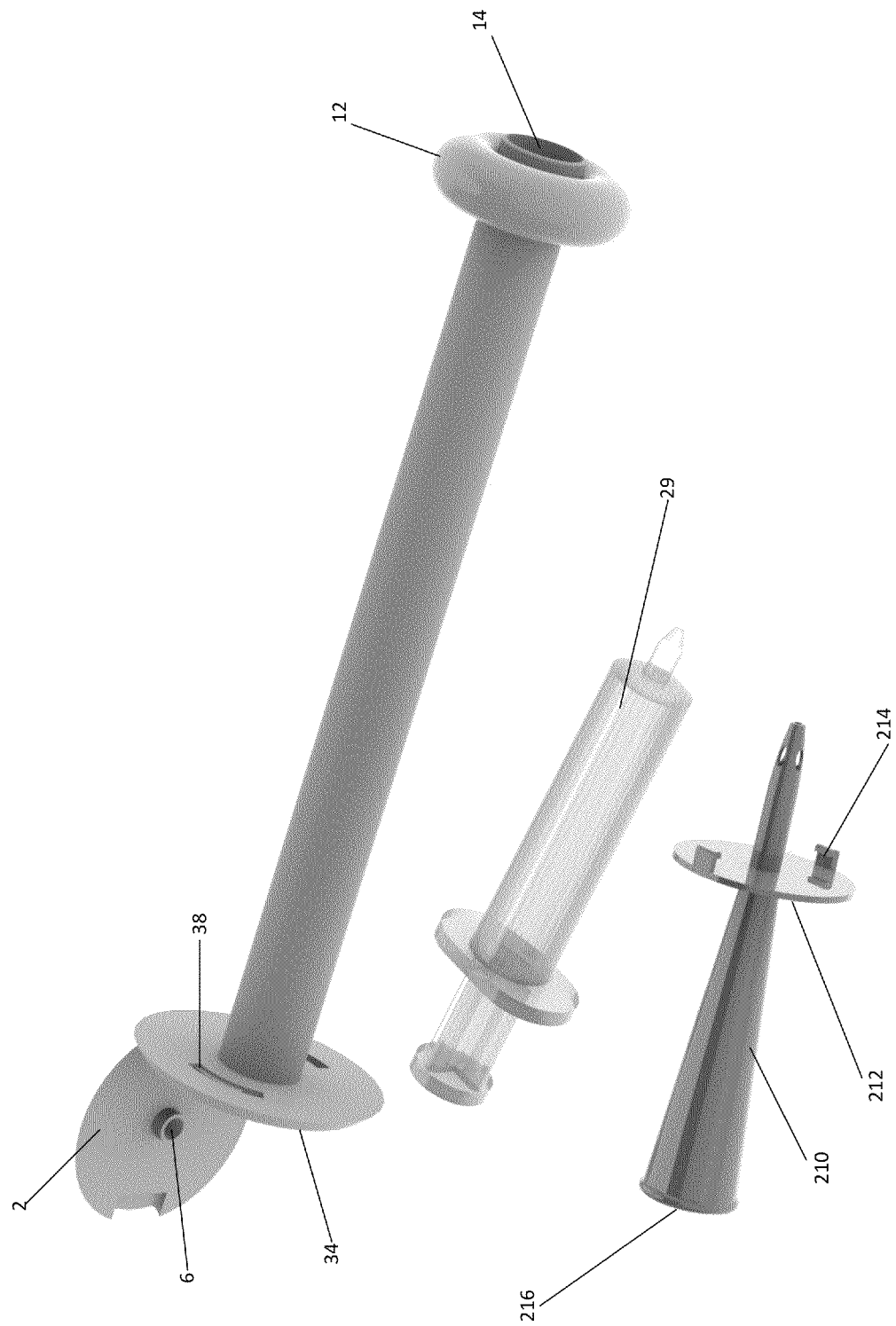
FIG. 37 illustrates an embodiment of the medical device with the first cap unsecured to the hollow tube, a syringe, and a universal connector
Figure 38:
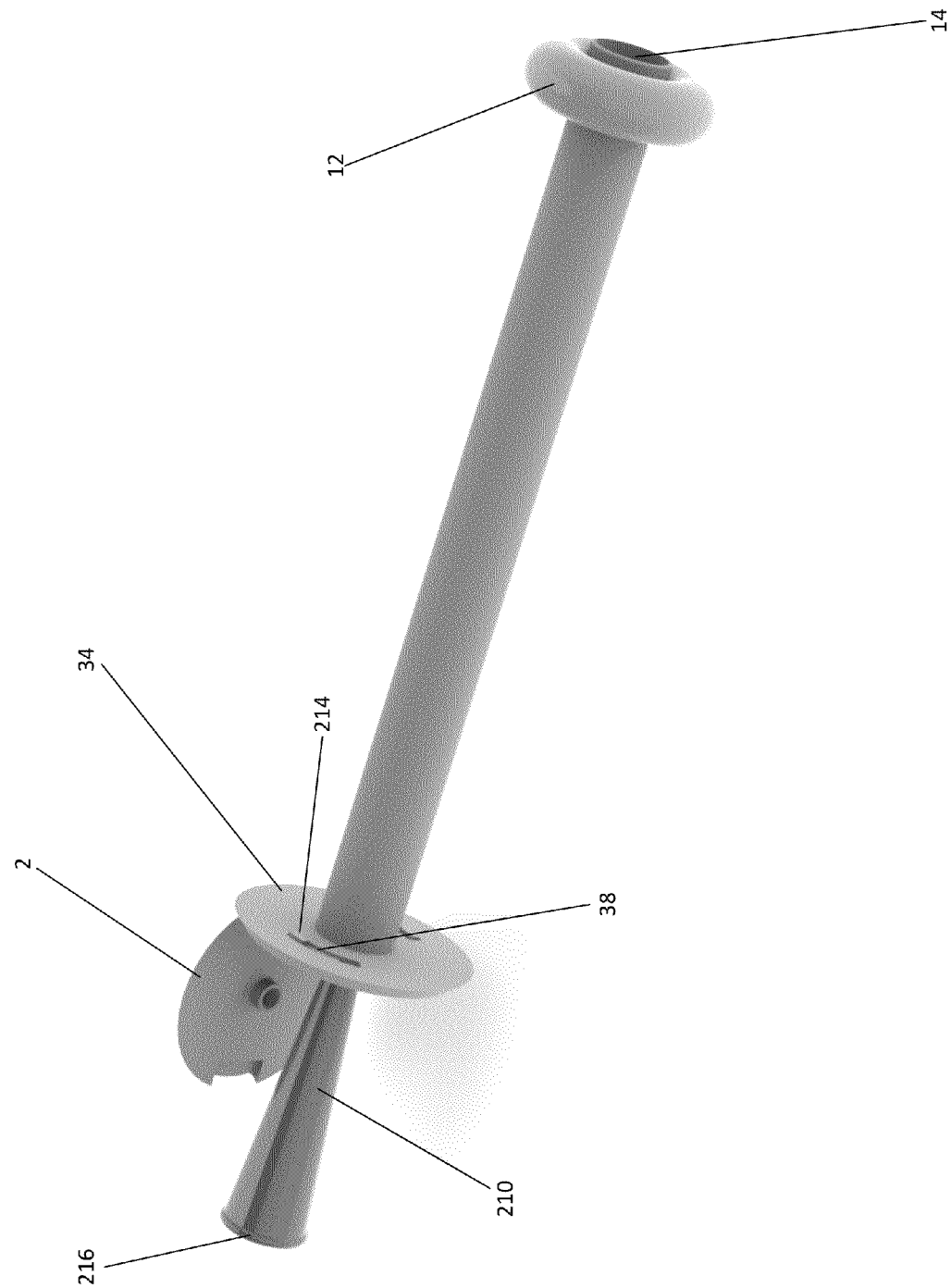
FIG. 38 illustrates an embodiment of the medical device with the first cap unsecured to the hollow tube and a universal connector operatively connected to the medical device through an embodiment of the locking mechanism.

Referring now to FIG. 36, FIG. 37 and FIG. 38 which disclose embodiments as previously discussed using like numbers and that are particularly suitable for insertion into a patient's kidney. A particular embodiment of the universal connector 210 is shown both prior to and after it has been operatively attached to an embodiment of the medical device. As shown in FIG. 38, the universal connector 210 can operatively attach to the medical device via engagement of the protrusions 214 from the engagement apparatus 212 with the twist locking mechanism 38.

While reference has been made to a patient throughout the specification it should be appreciated that that the patient could be any mammal.

EXAMPLE 1

A medical device of the present disclosure was placed into a previously existing suprapubic tract. A guide wire was placed through the device currently in place and the old device was removed over the wire. A depth gauge was placed over the guide wire until then end with a balloon was in the bladder and then the balloon was inflated. The patient's bladder was filled with water and the clamp on the surface of the depth gauge was clamped. The moveable surface lock on the depth gauge was moved to the skin surface while holding up on the depth gauge. The depth was measured. A matching size device of the present disclosure was selected. The depth gauge was removed and the selected device was placed over the wire and threaded into the bladder. The balloon-like component on the selected device was inflated following insertion into bladder. The bladder was drained after connecting drainage tubing via a locking mechanism to the inserted device. The drainage tubing was removed and the first cap was securely attached to the proximal end of the device. The patient was instructed on use of the inserted device and how often their bladder should be drained via the inserted device.

EXAMPLE 2

A medical device of the present disclosure was placed into a new patient by creating a new suprapubic tract. A cystoscope was placed via urethra into the bladder and the bladder was filled with liquid. An 18 gauge spinal needle was inserted into the patient approximately two fingerbreadths above the pubic symphisis in the midline until urine returned from the needle and needle was visualized through the cystoscope. A guide wire was threaded through the needle. The tract was dilated using an Amplatz balloon dilating system (but any means of dilating will work) to the desired French size. A depth gauge was placed over the wire until the balloon was in the bladder and the balloon was inflated. The patient's bladder was refilled and the depth gauge was clamped. The moveable surface lock on the depth gauge was moved to the patient's skin surface while holding up on the depth gauge and the depth was measured. A matching size device of the present disclosure was selected. The depth gauge was removed and the selected device was placed over the wire and threaded into the bladder. The balloon-like component on the selected device was inflated following insertion into bladder. The bladder was drained after connecting drainage tubing via a locking mechanism to the inserted device. The drainage tubing was removed and the first cap was securely attached to the proximal end of the device. The patient was instructed on use of the inserted device and how often their bladder should be drained via the inserted device.

Some embodiments have additional uses, for example, as a feeding tube via port-like access to a patient's stomach, i.e., a G-button. Or for port-like access to another internal cavity of a patient.

Some embodiments involve one or more parts of the urinary system. In some embodiments, the urinary system includes the kidneys, ureters, bladder, and urethra.

Those skilled in the art will appreciate that the present invention may be embodied by forms that are not disclosed without departing from the spirit or fundamental attributes thereof. While the present disclosure describes only some of the possible embodiments, a skilled artisan will appreciate that other variations are contemplated as being with the scope of the present invention. Accordingly, the present invention is not limited in the particular embodiments which have been described in detail therein. Since many embodiments of the invention can be made without departing from the spirit and scope of the invention, the invention resides in the claims hereinafter appended.

What is claimed is:
1. A medical device comprising:
 a continuous hollow tube, the length sized for spanning the distance between an exterior surface of a mammal and an interior cavity of the mammal's urinary system, the hollow tube having an open proximal end and an open distal end;

a first cap having a top surface and a bottom surface, the first cap being operatively configured for securely attaching to the proximal end of the tube;

a hollow flexible stem fluidly connecting the first cap and the proximal end of the hollow tube so that liquid may pass into the bottom surface of the first cap, through the hollow flexible stem and into a separate channel within the hollow tube; and an inflation port on the bottom surface of the cap.

2. The medical device of claim 1 wherein the continuous hollow tube has a diameter between 10 French and 40 French and the proximal end of the hollow tube is longitudinally more rigid than the distal end.

3. The medical device of claim 2 wherein the diameter of the continuous hollow tube is between 20 and 30 French.

4. The medical device of claim 2 wherein the diameter of the continuous hollow tube is greater than 30 French.

5. The medical device of claim 2 wherein the diameter of the continuous hollow tube is less than 20 French.

6. The medical device of claim 1 wherein the first cap covers the open proximal end of the tube when securely attached to the proximal end of the tube and the bottom surface of the cap is recessed within the proximal end of the tube upon secure attachment.

7. The medical device of claim 1 wherein the fluidly separate channel runs from the proximal end of the hollow tube toward the distal end of the hollow tube and the hollow flexible stem is permanently attached to the hollow tube below the open proximal end of the hollow tube.

8. The medical device of claim 1 wherein the inflation port is operatively configured to receive liquid via a syringe so when the cap is not securely attached to the proximal end of the tube liquid may be injected via the inflation port and travel from the cap, through the hollow flexible stem and down the separate channel within the hollow tube.

9. The medical device of claim 1 further comprising a second cap having top surface and a bottom surface that is operatively configured to securely attach to the proximal end of the tube, the second cap having at least one port from the top surface through to the bottom surface.

10. The medical device of claim 1 further comprising an inflatable balloon along the exterior surface of the hollow tube and in fluid communication with the inflation port via the separate channel within the hollow tube.

11. The medical device of claim 1 wherein the length of the continuous hollow tube is between a length between 0.8 cm and 15 cm.

12. The medical device of claim 1 wherein the length of the continuous hollow tube is greater than 8 cm.

13. The medical device of claim 1 wherein the length of the continuous hollow tube is less than 10 cm.

14. The medical device of claim 1 wherein the inflation port of the device sits at least partially beneath skin of the mammal after insertion of the device and when the cap is securely attached to the proximal end of the tube.

15. The medical device of claim 1:

wherein the continuous hollow tube has a diameter between 10 French and 40 French;

wherein the first cap covers the open proximal end of the tube when securely attached to the proximal end of the tube, the bottom surface of the cap being recessed within the proximal end of the tube upon secure attachment;

wherein the hollow flexible stem is permanently attached to the hollow tube below the open proximal end of the hollow tube and the separate channel runs from the proximal end of the hollow tube toward the distal end of the hollow tube; and wherein the inflation port is operatively configured to receive liquid via a syringe so when the cap is not securely attached to the proximal end of the tube liquid may be injected via the inflation port and travel from the cap, through the hollow flexible stem and down the separate channel within the hollow tube.

16. The medical device of claim 1 wherein the exterior surface of the mammal is the mammal's back and the interior cavity of the mammal's urinary system is the mammal's pelvis of its kidney.

17. The medical device of claim 16 further comprising a one way valve located within the tube of the medical device to prevent liquid from traveling from the mammal's kidney to the external surface of the mammal's skin when the first cap is not securely attached to the proximal end of the tube.

* * * * *